US008178752B1

(12) United States Patent
Tillman et al.

(10) Patent No.: US 8,178,752 B1
(45) Date of Patent: May 15, 2012

(54) PEANUT CULTIVAR UFT113

(75) Inventors: Barry Lawrence Tillman, Marianna, FL (US); Daniel Wayne Gorbet, Greenwood, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 0 days.

(21) Appl. No.: 13/159,645

(22) Filed: Jun. 14, 2011

(51) Int. Cl.
*A01H 5/00* (2006.01)
*A01H 5/10* (2006.01)
*A01H 1/00* (2006.01)
*A01H 3/04* (2006.01)

(52) U.S. Cl. ........ 800/298; 800/260; 800/278; 800/279; 800/288; 800/270; 800/265; 800/263

(58) Field of Classification Search ........................ None
See application file for complete search history.

(56) References Cited

U.S. PATENT DOCUMENTS

| | | | |
|---|---|---|---|
| 5,304,719 A | | 4/1994 | Segebart |
| 5,367,109 A | | 11/1994 | Segebart |
| 5,523,520 A | | 6/1996 | Hunsperger et al. |
| 5,684,232 A | * | 11/1997 | Horn et al. ..................... 800/298 |
| 5,763,755 A | | 6/1998 | Carlone |
| 5,850,009 A | | 12/1998 | Kevern |
| 5,850,028 A | | 12/1998 | Sebern |
| 5,945,578 A | | 8/1999 | Moore |
| 6,121,472 A | | 9/2000 | Knauft et al. |
| 7,923,605 B1 | | 4/2011 | Streit |

OTHER PUBLICATIONS

Eshed, Y. and Zamir, D., "Less-than-additive epistatic interactions of quantitative trait loci in tomato", *Genetics*, 1996, 143: 1807-1817.
Kraft, T., Hansen, M., and Nilsson, N. O., "Linkage disequilibrium and fingerprinting in sugar beet", *Theor. App. Genet.*, 2000, 101: 323-326.
Poehlman, J.M. and Sleper, D.A., "Breeding Field Crops", 4th Edition, Iowa State University Press, 1995, pp. 172-174.
Lee, T.A., et al., "Peanut Disease Atlas", Extension Plant Pathologists—The Texas A&M University System, http://165.91.154132/Texlab/Fiber/Peanuts/atlas-toc.html, Revised 1995, 6 pgs.
Culbreath, A., et al., "Peanut $R_x$, Minimizing Diseases of Peanut In The Southeastern United States", The 2010 Version of the Peanut Disease Risk Index, 16 pgs.
"Tospovirus", *Wikipedia, The free encyclopedia*, Wikimedia Foundation, Inc., Aug. 2, 2011, http://en.wikipedia.org/wiki/Tospovirus, 1 pg.
Culbreath, A.K., Todd, J.W., and Brown, S.L., "Epidemiology and Management of Tomato Spotted Wilt in Peanut", *Annu. Rev Phytopathol*, 2003, 41: 53-75.
Paul L. Hollis Farm Press Editorial Staff, "Tomato spotted wilt research paying dividends", Southeast Farm Press, Jan. 25, 2011, http://southeastfarmpress.com/print/peanuts/tomato-spotted-wilt-research-paying-dividends, 2 pgs.
Culbreath, A.K., et al., "High Levels of Field Resistance to Tomato spotted wilt virus in Peanut Breeding Lines Derived from *hypogaea* and *hirsuta* Botanical Varieties", *Peanut Science*, 2005, 32: 20-24.
Rowland, D., et al., "*Tomato spotted wilt virus* in peanut tissue types and physiological effects related to disease incidence and severity", *Plant Pathology*, 2005, 54: 431-440.
Knauft, D.A., Norden, A.J., and Gorbet, D.W., edited by FEHR, W.R., "Peanut", Principles of Cultivar Development, vol. 2, Crop Species, Chapter 10, MacMillan Publ. Co., 1986, pp. 346-384.
"Minimizing the effects of tomato spotted wilt of peanut using host plant resistance", TSTAR proposal, TSTAR-C FY2010, Mar. 16, 2010, 9 pgs.

* cited by examiner

*Primary Examiner* — Stuart F. Baum
(74) *Attorney, Agent, or Firm* — Jondle & Associates, P.C.

(57) ABSTRACT

A peanut cultivar designated UFT113 is disclosed. The invention relates to the seeds, the plants, and the plant parts of peanut cultivar UFT113, and to methods for producing a peanut plant by crossing peanut cultivar UFT113 with itself or with another peanut variety. The invention also relates to methods for producing a peanut plant containing in its genetic material one or more transgenes and to the transgenic peanut plants and plant parts produced by those methods. This invention also relates to peanut cultivars, or breeding cultivars, and plant parts derived from peanut cultivar UFT113, to methods for producing other peanut cultivars, lines or plant parts derived from peanut cultivar UFT113, and to the peanut plants, varieties, and their parts derived from use of those methods. The invention further relates to hybrid peanut seeds, plants, and plant parts produced by crossing cultivar UFT113 with another peanut cultivar.

27 Claims, No Drawings

PEANUT CULTIVAR UFT113

BACKGROUND OF THE INVENTION

The present invention relates to a new and distinctive peanut (Arachis hypogaea L.) variety, designated UFT113. All publications cited in this application are herein incorporated by reference.

The peanut is an annual herbaceous plant of the legume family. Originally cultivated in South America and the eastern slopes of the Andes mountains, peanut is now grown worldwide in the tropic and temperate zones and is recognized as one of the major oilseed crops and as a rich source of protein.

The peanut plant grows best in light, sandy soil and requires four to five months of warm weather and an annual rainfall of 20 to 39 inches, or the equivalent in irrigation water. The pea-like yellow flowers form in axillary clusters and only bloom for a short time. Following self-pollination, the stalk at the base of the ovary, called the pedicel, elongates rapidly and turns downward to bury the fruits one to several inches below the ground surface. The peanut pods complete their development 120 to 150 days after planting. During harvest, the entire plant including the roots is removed from the soil.

Peanut is an important and valuable crop. Peanut is particularly susceptible to viruses and fungi during growth and storage. Indeed, diseases are major constraints to peanut production worldwide.

In the United States, spotted wilt can be considered an invasive disease of peanut caused by the pathogen Tomato Spotted Wilt Tospovirus (TSWV) (Demski, J. W. and D. V. R. Reddy, *Tomato spotted wilt and peanut bud necrosis*. Compendium of Peanut Diseases, $2^{nd}$ Edition, pp. 53-54 (1997)). The disease is transferred to plants by thrips carrying the virus, the two most common species being Tobacco thrips (*Frankliniella fusca*) and Western flower thrips (*Frankliniella occidentalis*). These tiny insects are also referred to as thunderflies, thunderbugs, storm flies, thunderblights, and corn lice. While there are still unknown factors influencing the incidence of TSWV, research has shown that planting date, plant population, row patterns, and tillage can affect the severity of disease.

The initial symptoms of spotted wilt can appear as early as 21 days after the seedlings emerge. Early symptoms include brown speckles on the underside of leaves, along with yellow ring-spotting and mottling on the upperside of the leaf. Leaves may also be wilted or flaccid, and new leaves are about half their normal size, crinkled, and display a range of symptoms including chlorosis, concentric chlorotic ring-spots, ring-spots with green centers, chlorotic line patterns, and general mottling. A downward twisting of leaf petioles and some terminals can also be seen at this stage. Brown, necrotic spots or streaks may also be present on the leaf petiole and stem. Stunting is commonly observed on plants infected at the seedling stage, and few pods are set. Seeds that are produced by TSWV infected plants are smaller than normal and have mottled red to brown seed coats that are often cracked, and show poor germination. Late season TSWV infections are characterized by a decline in plant vigor, yellowing of the foliage, and collapse of the vines. Faint ring-spot or line patterns may be seen on the youngest leaves, and the root systems of these plants are often discolored and partially rotted. Severe infections may result in plant death.

Since the mid 1990's, TSWV has caused severe economic losses on peanut crops in Florida and other parts of the southeastern United States (Culbreath et al., *Epidemiology and management of tomato spotted wilt in peanut*. Annual Review of Phytopathology 41:53-75 (2003)). Peanut yield losses to spotted wilt can be significant. If 50% of the row feet are showing symptoms of TSWV, research shows that 1,000 to 2,000 pounds of yield per acre will be lost. In addition to this, control measures to reduce crop losses have had significant negative impacts on peanut production. Prior to TSWV, the normal seeding density was three to four seeds per foot of row, but to reduce TSWV the seeding density has been increased to six to seven seeds per foot of row, effectively doubling seed costs. Similarly, before TSWV the peanut crop was planted during April and early May. To reduce the effects of TSWV, the vast majority of the peanut crop is now planted between May $10^{th}$ and June $1^{st}$. This delayed planting causes conflicts with production of cotton, the major rotational crop with peanut, and shortens the planting window due to constraints of cool weather in the fall months. Because peanut requires an average of 140 days until harvest, later planting reduces yield potential and increases the danger of frost damage in the fall.

Although the date of planting and seeding density has been important in reducing losses from spotted wilt, the most effective control measure is cultivar resistance. Thus, a continuing goal of peanut plant breeders is to develop stable, high yielding peanut cultivars that are agronomically sound to maximize the yield produced on the land. To accomplish this goal, the peanut breeder must select and develop peanut plants that have the traits that result in superior cultivars. Several cultivars with moderate resistance to spotted wilt have been developed, but none have sufficient resistance to allow a return to April planting and a seeding density of three to four seeds per foot. If the planting window could be returned to April through May, farmers would have significantly more flexibility to plan their operations around weather and cotton production. Therefore, finding new sources and greater levels of resistance to TSWV is highly desirable.

There are numerous steps in the development of any novel, desirable plant germplasm. Plant breeding begins with the analysis, definition of problems and weaknesses of the current germplasm, the establishment of program goals, and the definition of specific breeding objectives. The next step is selection of germplasm that possesses the traits to meet the program goals. The goal is to combine in a single variety or hybrid an improved combination of desirable traits from the parental germplasm. These important traits may include improved flavor, higher yield, high oleic acid, improved color, resistance to diseases and insects, tolerance to drought and heat, and better agronomic quality.

Methods for producing novel peanut lines through selection are known in the art. Each of the following references is incorporated in its entirety, herein, by reference: Moore, K. M. et al., *J. Heredity* 80(3): 252 (1989); Norden, A. J., *Peanuts, Culture and Uses*. Am. Peanut Res. And Educ. Soc., Stillwater, Okla. (C. T. Wilson ed. 1973); Norden, A. J. in *Hybridization of Crop Plants* (H. H. Hadley ed. 1980); Norden, A. J., et al., Breeding of the cultivated peanut in *Peanut Science and Technology*, (H. E. Pattee ed. 1992); Norden, A. J. et al., *Florida Agr. Res.* 3:16-18 (1984); Knauft, D. A. et al., Peanut, *Peanut Principles of Cultivar Development*, 2:346-384 (Walter R. Fehr ed. 1987).

The foregoing examples of the related art and limitations related therewith are intended to be illustrative and not exclusive. Other limitations of the related art will become apparent to those of skill in the art upon a reading of the specification.

SUMMARY OF THE INVENTION

The following embodiments and aspects thereof are described in conjunction with systems, tools, and methods which are meant to be exemplary and illustrative, not limiting in scope. In various embodiments, one or more of the above-described problems have been reduced or eliminated, while other embodiments are directed to other improvements.

According to the invention, there is provided a novel peanut cultivar designated UFT113. This invention thus relates to the seeds of peanut cultivar UFT113, to the plants and plant parts of peanut cultivar UFT113 and to methods for producing a peanut plant by crossing peanut cultivar UFT113 with itself or another peanut plant, wherein the first or second peanut plant is the peanut plant from cultivar UFT113. Further, both first and second parent peanut plants may be from cultivar UFT113. Therefore, any methods using peanut cultivar UFT113 are part of this invention: selfing, backcrosses, hybrid breeding, and crosses to populations. Any plants produced using peanut cultivar UFT113 as at least one parent are within the scope of this invention.

This invention is also directed to methods for producing a peanut plant containing in its genetic material one or more transgenes and to the transgenic peanut plants produced by that method. This invention also relates to methods for producing other peanut cultivars derived from peanut cultivar UFT113 and to the peanut cultivar derived by the use of those methods. This invention further relates to hybrid peanut seeds and plants produced by crossing peanut cultivar UFT113 with another peanut line.

In another aspect, the present invention provides regenerable cells for use in tissue culture of peanut cultivar UFT113. The tissue culture will preferably be capable of regenerating plants having essentially all of the physiological and morphological characteristics of the foregoing peanut plant, and of regenerating plants having substantially the same genotype as the foregoing peanut plant. Preferably, the regenerable cells in such tissue cultures will be callus, protoplasts, meristematic cells, leaves, pollen, embryos, roots, root tips, anthers, pistils, flowers, seeds, petioles and suckers. Still further, the present invention provides peanut plants regenerated from the tissue cultures of the invention.

Another aspect of the invention is to provide methods for producing other peanut plants derived from peanut cultivar UFT113. Peanut cultivars derived by the use of those methods are also part of the invention.

The invention also relates to methods for producing a peanut plant containing in its genetic material one or more transgenes and to the transgenic peanut plant produced by those methods.

In another aspect, the present invention provides for single gene converted plants of UFT113. The single transferred gene may preferably be a dominant or recessive allele. Preferably, the single transferred gene will confer such traits as male sterility, herbicide resistance, insect resistance, modified fatty acid metabolism, modified carbohydrate metabolism, resistance for bacterial, fungal, or viral disease, male fertility, enhanced nutritional quality and industrial usage or the transferred gene will have no apparent value except for the purpose of being a marker for variety identification. The single gene may be a naturally occurring peanut gene or a transgene introduced through genetic engineering techniques.

The invention further provides methods for developing peanut plant in a peanut plant breeding program using plant breeding techniques including recurrent selection, backcrossing, pedigree breeding, restriction fragment length polymorphism enhanced selection, genetic marker enhanced selection and transformation. Seeds, peanut plants, and parts thereof, produced by such breeding methods are also part of the invention.

In addition to the exemplary aspects and embodiments described above, further aspects and embodiments will become apparent by reference by the study of the following descriptions.

DETAILED DESCRIPTION OF THE INVENTION

In the description and tables which follow, a number of terms are used. In order to provide a clear and consistent understanding of the specification and claims, including the scope to be given such terms, the following definitions are provided:

Allele. An allele is any of one or more alternative form of a gene, all of which relate to one trait or characteristic. In a diploid cell or organism, the two alleles of a given gene occupy corresponding loci on a pair of homologous chromosomes.

Alter. The utilization of up-regulation, down-regulation, or gene silencing.

*Arachis hypogea* L. The domesticated peanut, or groundnut, is an amphidiploid species in the legume or "bean" family and is an annual herbaceous plant.

Backcrossing. Backcrossing is a process in which a breeder repeatedly crosses progeny back to one of the parents one or more times. Backcrossing can be used to introduce one or more locus conversion from one genetic background into another.

Cell. Cell as used herein includes a plant cell, whether isolated, in tissue culture or incorporated in a plant or plant part.

Cotyledon. A cotyledon is a type of seed leaf. The cotyledon contains the food storage tissues of the seed.

Chlorosis. Used to describe a reduced amount of chlorophyll resulting in light or yellow colored leaves.

Concentric chlorotic ring-spots. Light or dark areas on the leaf in the form concentric circles, ovals, or similar shape not necessarily symmetrical or uniform in appearance.

Consumable. Means material that is edible by humans.

Diploid. A cell or organism having two sets of chromosomes.

Embryo. The embryo is the small plant contained within a mature seed.

Essentially all the physiological and morphological characteristics. A plant having essentially all the physiological and morphological characteristics of the recurrent parent, except for the characteristics derived from the converted gene.

Flower. As used herein, refers all parts of the flower, including but not limited to, stigma, style, ovary, anther, filament, corolla, and calyx.

Gene. As used herein, "gene" refers to a segment of nucleic acid. A gene can be introduced into a genome of a species, whether from a different species or from the same species, using transformation or various breeding techniques.

Gene Silencing. The interruption or suppression of the expression of a gene at the level of transcription or translation.

Genotype. Refers to the genetic constitution of a cell or organism.

Habit. This refers to the physical appearance of a plant. In peanuts, it can be prostrate, decumbent, semi-erect, or erect.

Hilum. This refers to the scar left on the seed which marks the place where the seed was attached to the pod prior to it (the seed) being harvested.

Leaflets. These are part of the plant shoot, and they manufacture food for the plant by the process of photosynthesis.

Leaf petiole. The small stalk attaching the leaf blade to the stem.

Leaf spots. A spot on a leaf usually resultant from infection; can be either chlorotic or necrotic and may be ringed, referred to as a ring-spot.

Linkage. Refers to a phenomenon wherein alleles on the same chromosome tend to segregate together more often than expected by chance if their transmission was independent.

Linkage disequilibrium. Refers to a phenomenon wherein alleles tend to remain together in linkage groups when segregating from parents to offspring, with a greater frequency than expected from their individual frequencies.

Locus. A locus confers one or more traits such as, for example, male sterility, herbicide tolerance, insect resistance, disease resistance, waxy starch, modified fatty acid metabolism, modified phytic acid metabolism, modified carbohydrate metabolism, and modified protein metabolism. The trait may be, for example, conferred by a naturally occurring gene introduced into the genome of the variety by backcrossing, a natural or induced mutation, or a transgene introduced through genetic transformation techniques. A locus may comprise one or more alleles integrated at a single chromosomal location.

Maturity Date. Plants are considered mature when about 70% of the pods display a dark brown or black endocarp on the middle upper side of the pod. The endocarp is revealed by removing the exocarp by mechanical scraping or by pressurized water.

Mottling. Abnormal coloration on plants, usually a sign of disease or malnutrition.

Peanut. The seed of a peanut plant, also known as earthnuts, ground nuts, goober peas, monkey nuts, pygmy nuts, and pig nuts.

Peanut flour. Flour high in protein, often used as a gluten-free solution.

Peanut oil. Often used in cooking, it has a mild flavour, high smoke point, and high monounsaturated content. Variations include aromatic roasted peanut oil, refined peanut oil, extra virgin or cold pressed peanut oil, and peanut extract.

Peanut Rx. An index designed to help growers approximate the magnitude of the risk that they face from diseases in the coming season.

Pedigree Distance. Relationship among generations based on their ancestral links as evidenced in pedigrees. May be measured by the distance of the pedigree from a given starting point in the ancestry.

Percent Identity. Percent identity as used herein refers to the comparison of the homozygous alleles of two peanut varieties. Percent identity is determined by comparing a statistically significant number of the homozygous alleles of two developed varieties. For example, a percent identity of 90% between peanut variety 1 and peanut variety 2 means that the two varieties have the same allele at 90% of their loci.

Percent Similarity. Percent similarity as used herein refers to the comparison of the homozygous alleles of a peanut variety such as peanut cultivar UFT113 with another plant, and if the homozygous allele of peanut cultivar UFT113 matches at least one of the alleles from the other plant, then they are scored as similar. Percent similarity is determined by comparing a statistically significant number of loci and recording the number of loci with similar alleles as a percentage. A percent similarity of 90% between peanut cultivar UFT113 and another plant means that peanut cultivar UFT113 matches at least one of the alleles of the other plant at 90% of the loci.

Plant. As used herein, the term "plant" includes reference to an immature or mature whole plant, including a plant from which seed, grain, or anthers have been removed. Seed or embryo that will produce the plant is also considered to be the plant.

Plant Height. Plant height is taken from the top of the soil to the top node of the plant and is measured in centimeters.

Plant Parts. As used herein, the term "plant parts" (or a part thereof) includes but is not limited to protoplasts, leaves, stems, roots, root tips, anthers, pistils, seed, embryo, pollen, ovules, cotyledon, hypocotyl, pod, flower, shoot, tissue, petiole, cells, meristematic cells, and the like.

Pod. This refers to the fruit of a peanut plant. It consists of the hull or shell (pericarp) and the peanut seeds.

Progeny. As used herein, includes an $F_1$ peanut plant produced from the cross of two peanut plants where at least one plant includes peanut cultivar UFT113 and progeny further includes, but is not limited to, subsequent $F_2$, $F_3$, $F_4$, $F_5$, $F_6$, $F_7$, $F_8$, $F_9$, and $F_{10}$ generational crosses with the recurrent parental line.

Protein Percent. Peanut seeds contain a considerable amount of protein. Protein is generally measured by NIR spectrophotometry and is reported as percentage basis.

Quantitative Trait Loci. Quantitative Trait Loci (QTL) refers to genetic loci that control to some degree, numerically representable traits that are usually continuously distributed.

Regeneration. Regeneration refers to the development of a plant from tissue culture.

Resistance. The intrinsic ability of a plant to prevent infection of disease.

Single gene converted. Single gene converted or conversion plant refers to plants which are developed by backcrossing, or via genetic engineering, wherein essentially all of the desired morphological and physiological characteristics of a line are recovered in addition to the single gene transferred into the line via the backcrossing technique or via genetic engineering.

Spotted wilt. A disease of peanut caused by the Tomato Spotted Wilt Virus

Subline. Although peanut cultivar UFT113 contains substantially fixed genetics, and is phenotypically uniform and with no off-types expected, there still remains a small proportion of segregating loci either within individuals or within the population as a whole. A breeder of ordinary skill in the art may fix these loci by making them more uniform in order to optimize the performance of the variety. One example of this type of approach is described in the "breeding bias" methods described in U.S. Pat. No. 5,437,697 and may be utilized by a breeder of ordinary skill in the art to further purify the variety in order to increase its yield. By sublining in this manner, no crosses to a different variety are made, and so a new genetic variety is not created and the overall genetic composition of the variety remains essentially the same.

Thrips. Tiny insects which carry and transmit disease. The two most common species being Tobacco thrips (*Frankliniella fusca*) and Western flower thrips (*Frankliniella occidentalis*). They are also referred to as thunderflies, thenderbugs, storm flies, thrunderblights, and corn lice.

Tolerance. The intrinsic ability of a plant to withstand infection of disease.

Tomato Spotted Wilt Tospovirus (TSWV). A class V virus having a single stranded RNA genome with negative polarity found within the family Bunyaviridae. TSWV is an arbovirus usually vectored by thrips and is common in warm climates such as Asia, America, Europe and Africa.

Total Sound Mature Kernels (TSMK). The percentage of SMK (sound mature kernels) riding a screen with 0.64 by 1.91 cm slots plus sound splits (i.e. the sum of SMK and sound splits).

Variety. Synonymous with cultivar, a substantially homozygous peanut line minor modifications thereof that retain the overall genetics of the peanut line including but not limited to a subline, a locus conversion, a mutation, a transgene, or a somaclonal variant.

Peanut Cultivar UFT113 is a runner-type variety with exceptional resistance to spotted wilt caused by Tomato Spotted Wilt Virus. Additionally, Peanut Cultivar UFT113 has large seed that place it in the upper range of runner-type cultivars. Peanut Cultivar UFT113 has excellent TSMK. Peanut cultivar UFT113 has very high yield potential when compared to lines of similar maturity especially in the presence of spotted wilt and has excellent agronomic characteristics including a prominent center stem and runner growth (prostrate) habit.

Some of the selection criteria used for various generations include: pod yield, grade, seed size, disease resistance, seedling emergence, disease tolerance, maturity, and late season plant intactness.

The cultivar has shown uniformity and stability, as described in the following variety description information. It has been self-pollinated a sufficient number of generations with careful attention to uniformity of plant type. The line has been increased with continued observation for uniformity.

Peanut cultivar UFT113 has the following morphologic and other characteristics (based primarily on data collected in Marianna, Fla.

TABLE 1

VARIETY DESCRIPTION INFORMATION

Plant:

Growth habit: Prostrate
Flowering on the main stem: Mixed
Branching pattern: Alternate
Branching: Profuse
Maturity:

Region: Florida, United States
Number of days to maturity: 140 to 145
Days earlier than comparison peanut line DP-1: 5 to 10
Days later than comparison peanut line Georgia Green: 5 to 10
Leaves:

Arrangement: Opposite, pinnate, usually 4-foliolate
Leaflet length: 51.8 mm
Leaflet length/width ratio: 2.3 mm
Flower:

Flower color: Yellow
Days to flower: 25 to 35; indeterminate
Arrangement: Axillary; from leaf axil
Pod:

Shape: oblong, indehiscent legume
Length: 35.5 mm
Diameter: 13.3 mm
Number of seeds per pod: 2 to 3
Pod yield (KG/HA): 3000 to 5000
Surface: Glabrous
Constriction: Shallow to medium
Beak: Inconspicuous to pronounced
% pod splitting: None observed
Seed:

Coat color: Tan
Coat surface: Smooth
Shape: Elongated
Length: 18.1 mm
Width: 9.9 mm
Grams per 100 seeds (8% moisture): 77.2 g TABLE 1-continued

VARIETY DESCRIPTION INFORMATION

Disease resistance:

Southern Stem Rot: Moderately resistant
Late Leaf Spot: Susceptible
Spotted Wilt: Resistant
Tomato Spotted Wilt Virus Infection: Resistant Peanut cultivar UFT113 is similar to peanut cultivar DP-1. While similar to peanut cultivar DP-1 there are numerous differences including: 1) maturity; UFT113 matures about 5-10 days sooner than DP-1, 2) seed size; seed of UFT113 are larger than seed of DP-1, and 3) the plant height of UFT113 is greater than that of DP-1.

Peanut cultivar UFT113 is similar to peanut cultivar Georgia Green. While similar to peanut cultivar Georgia Green there are numerous differences including: 1) maturity; UFT113 matures about 5-10 days later than Georgia Green, 2) seed size; seed of UFT113 are larger than seed of Georgia Green, and 3) the plant height of UFT113 is greater than that of Georgia Green.

Peanut cultivar UFT113 is similar to commercial cultivar Florida-07, however, there are several differences. Peanut cultivar UFT113 has normal oleic acid oil whereas Florida-07 has high oleic acid oil. Additionally, peanut cultivar UFT113 has a high level of resistance to spotted wilt and infection by TSWV, while Florida-07 has moderate tolerance to spotted wilt and is more susceptible to infection by TSWV.

Further Embodiments of the Invention

The advent of new molecular biological techniques has allowed the isolation and characterization of genetic elements with specific functions, such as encoding specific protein products. Scientists in the field of plant biology developed a strong interest in engineering the genome of plants to contain and express foreign genetic elements, or additional, or modified versions of native or endogenous genetic elements in order to alter the traits of a plant in a specific manner. Any DNA sequences, whether from a different species or from the same species, which are introduced into the genome using transformation or various breeding methods are referred to herein collectively as "transgenes."

Additional methods include genetic engineering and mutagenesis of peanut cultivar UFT113. Examples include, but are not limited to, expression vectors introduced into plant tissues using a direct gene transfer method, such as microprojectile-mediated delivery, DNA injection, electroporation, and the like. More preferably, expression vectors are introduced into plant tissues by using either microprojectile-mediated delivery with a biolistic device or by using *Agrobacterium*-mediated transformation. Transformant plants obtained with the protoplasm of the invention are intended to be within the scope of this invention.

In some embodiments of the invention, a transgenic variant of peanut cultivar UFT113 may contain at least one transgene but could contain at least 1, 2, 3, 4, 5, 6, 7, 8, 9, 10, and/or no more than 15, 14, 13, 12, 11, 10, 9, 8, 7, 6, 5, 4, 3, or 2. Over the last fifteen to twenty years several methods for producing transgenic plants have been developed, and the present invention also relates to transgenic variants of the claimed peanut variety UFT113.

Nucleic acids or polynucleotides refer to RNA or DNA that is linear or branched, single or double stranded, or a hybrid thereof. The term also encompasses RNA/DNA hybrids.

These terms also encompass untranslated sequence located at both the 3' and 5' ends of the coding region of the gene: at least about 1000 nucleotides of sequence upstream from the 5' end of the coding region and at least about 200 nucleotides of sequence downstream from the 3' end of the coding region of the gene. Less common bases, such as inosine, 5-methylcytosine, 6-methyladenine, hypoxanthine and others can also be used for antisense, dsRNA and ribozyme pairing. For example, polynucleotides that contain C-5 propyne analogues of uridine and cytidine have been shown to bind RNA with high affinity and to be potent antisense inhibitors of gene expression. Other modifications, such as modification to the phosphodiester backbone, or the 2'-hydroxy in the ribose sugar group of the RNA can also be made. The antisense polynucleotides and ribozymes can consist entirely of ribonucleotides, or can contain mixed ribonucleotides and deoxyribonucleotides. The polynucleotides of the invention may be produced by any means, including genomic preparations, cDNA preparations, in vitro synthesis, RT-PCR, and in vitro or in vivo transcription.

One embodiment of the invention is a process for producing peanut variety UFT113 further comprising a desired trait, said process comprising introducing a transgene that confers a desired trait to a peanut plant of variety UFT113. Another embodiment is the product produced by this process. In one embodiment the desired trait may be one or more of herbicide resistance, insect resistance, disease resistance, decreased phytate, or modified fatty acid or carbohydrate metabolism. The specific gene may be any known in the art or listed herein, including: a polynucleotide conferring resistance to imidazolinone, dicamba, sulfonylurea, glyphosate, glufosinate, triazine, benzonitrile, cyclohexanedione, phenoxy proprionic acid, and L-phosphinothricin; a polynucleotide encoding a *Bacillus thuringiensis* polypeptide; a polynucleotide encoding phytase, FAD-2, FAD-3, galactinol synthase, or a raffinose synthetic enzyme; or a polynucleotide conferring resistance to rust (*Puccinia arachidis*), early and late leaf spot (*Cercospora arachidicola* and *Cercosporidium personatum*), web blotch (*Didymella arachidicola*), pepper spot (*Leptosphaerulina crassiasca*), TSWV, atmospheric scorch, chemical burn, iron chlorosis, potato leafhopper (*Empoasca fabae*) seedling disease (*Rhizoctonia solani, Pythium* spp., *Fusarium* spp. and others), yellow mold (*Aspergillus flavus, Aspergillus parasiticus*), root knot nematode (*Meloidogyne arenaria*) root lesion nematode, southern blight (*Sclerotium rolfsii*), sclerotinia blight (*Sclerotinia minor*), Rhizoctonia pod, peg and limb rot (*Rhizoctonia solani*), pythium pod rot (*Pythium myriotylum*), botrytis blight (*Botrytis cinerea*), black mold (*Aspergillus niger*), blackhull (*Thielaviopsis basicola*), phymatotrichum root rot (*Phymatotrichum omnivorum*), and tooth fungus (*Phanerochaeta* sp).

Methods for transformation and regeneration of peanut cells are known, such as those described in Ozias-Akins, P. et al., *Plant Science* 93:185-194 (1993), Norden, A. J., et al., chapter 4, supra. In addition, specific genes associated with improved peanut traits may be introduced using peanut transformation methods known in the art (Ozias-Akins, P., et al., *Plant Science* 93:185-194 (1993)). One means to obtain peanut oil with a higher percentage of unsaturated fatty acids is through the genetic engineering of plants, such as that described in U.S. Pat. No. 5,510,255 to Knauf, et al. 1996. Additional methods for plant transformation have been developed, including biological and physical plant transformation protocols. See, for example, Miki et al., "Procedures for Introducing Foreign DNA into Plants," in *Methods in Plant Molecular Biology and Biotechnology*, Glick and Thompson Eds., CRC Press, Inc., Boca Raton, pp. 67-88 (1993), and Armstrong, "The First Decade of Maize Transformation: A Review and Future Perspective," *Maydica*, 44:101-109 (1999). In addition, expression vectors and in vitro culture methods for plant cell or tissue transformation and regeneration of plants are available. See, for example, Gruber, et al., "Vectors for Plant Transformation," in *Methods in Plant Molecular Biology and Biotechnology*, Glick and Thompson Eds., CRC Press, Inc., Boca Raton, pp. 89-119 (1993).

A genetic trait which has been engineered into the genome of a particular peanut plant may then be moved into the genome of another variety using traditional breeding techniques that are well known in the plant breeding arts. For example, a backcrossing approach is commonly used to move a transgene from a transformed peanut variety into an already developed peanut variety, and the resulting backcross conversion plant would then comprise the transgene(s).

Various genetic elements can be introduced into the plant genome using transformation. These elements include, but are not limited to, genes, coding sequences, inducible, constitutive and tissue specific promoters, enhancing sequences, and signal and targeting sequences. For example, see the traits, genes, and transformation methods listed in U.S. Pat. No. 6,118,055.

Plant transformation involves the construction of an expression vector which will function in plant cells. Such a vector comprises DNA comprising a gene under control of, or operatively linked to, a regulatory element (for example, a promoter). The expression vector may contain one or more such operably linked gene/regulatory element combinations. The vector(s) may be in the form of a plasmid and can be used alone or in combination with other plasmids to provide transformed peanut plants using transformation methods as described below to incorporate transgenes into the genetic material of the peanut plant(s).

Expression Vectors for Peanut Transformation: Marker Genes

Expression vectors include at least one genetic marker operably linked to a regulatory element (for example, a promoter) that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well known in the transformation arts, and include, for example, genes that code for enzymes that metabolically detoxify a selective chemical agent which may be an antibiotic or an herbicide, or genes that encode an altered target which is insensitive to the inhibitor.

One commonly used selectable marker gene for plant transformation is the neomycin phosphotransferase II (nptII) gene which, when under the control of plant regulatory signals, confers resistance to kanamycin. Fraley, et al., Proc. Natl. Acad. Sci. USA, 80:4803 (1983). Another commonly used selectable marker gene is the hygromycin phosphotransferase gene which confers resistance to the antibiotic hygromycin. Vanden Elzen, et al., Plant Mol. Biol., 5:299 (1985).

Additional selectable marker genes of bacterial origin that confer resistance to antibiotics include gentamycin acetyl transferase, streptomycin phosphotransferase and aminoglycoside-3'-adenyl transferase, the bleomycin resistance determinant (Hayford, et al., Plant Physiol., 86:1216 (1988); Jones, et al., Mol. Gen. Genet., 210:86 (1987); Svab, et al., Plant Mol. Biol., 14:197 (1990); Hille, et al., Plant Mol. Biol., 7:171 (1986)). Other selectable marker genes confer resistance to herbicides such as glyphosate, glufosinate, or bromoxynil (Comai, et al., Nature, 317:741-744 (1985); Gordon- Kamm, et al., Plant Cell, 2:603-618 (1990); Stalker, et al., Science, 242:419-423 (1988)).

Selectable marker genes for plant transformation not of bacterial origin include, for example, mouse dihydrofolate reductase, plant 5-enolpyruvylshikimate-3-phosphate synthase, and plant acetolactate synthase (Eichholtz, et al., Somatic Cell Mol. Genet., 13:67 (1987); Shah, et al., Science, 233:478 (1986); Charest, et al., Plant Cell Rep., 8:643 (1990)).

Another class of marker genes for plant transformation requires screening of presumptively transformed plant cells, rather than direct genetic selection of transformed cells, for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening presumptively transformed cells include β-glucuronidase (GUS), β-galactosidase, luciferase, and chloramphenicol acetyltransferase (Jefferson, R. A., Plant Mol. Biol. Rep., 5:387 (1987); Teeri, et al., EMBO J., 8:343 (1989); Koncz, et al., Proc. Natl. Acad. Sci. USA, 84:131 (1987); DeBlock, et al., EMBO J., 3:1681 (1984)).

In vivo methods for visualizing GUS activity that do not require destruction of plant tissue are available (Molecular Probes, Publication 2908, IMAGENE GREEN, pp. 1-4 (1993); Naleway, et al., J. Cell Biol., 115:151a (1991)). However, these in vivo methods for visualizing GUS activity have not proven useful for recovery of transformed cells because of low sensitivity, high fluorescent backgrounds, and limitations associated with the use of luciferase genes as selectable markers. A gene encoding Green Fluorescent Protein (GFP) has been utilized as a marker for gene expression in prokaryotic and eukaryotic cells (Chalfie, et al., Science, 263:802 (1994)). GFP and mutants of GFP may be used as screenable markers.
Expression Vectors for Peanut Transformation: Promoters Genes included in expression vectors must be driven by a nucleotide sequence comprising a regulatory element (for example, a promoter). Several types of promoters are well known in the transformation arts as are other regulatory elements that can be used alone or in combination with promoters.

As used herein, "promoter" includes reference to a region of DNA upstream from the start of transcription and involved in recognition and binding of RNA polymerase and other proteins to initiate transcription. A "plant promoter" is a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred." Promoters that initiate transcription only in a certain tissue are referred to as "tissue-specific." A "cell-type" specific promoter primarily drives expression in certain cell types in one or more organs, for example, vascular cells in roots or leaves. An "inducible" promoter is a promoter which is under environmental control. Examples of environmental conditions that may effect transcription by inducible promoters include anaerobic conditions or the presence of light. Tissue-specific, tissue-preferred, cell-type specific, and inducible promoters constitute the class of "non-constitutive" promoters. A "constitutive" promoter is a promoter that is active under most environmental conditions.

A. Inducible Promoters—An inducible promoter is operably linked to a gene for expression in peanut. Optionally, the inducible promoter is operably linked to a nucleotide sequence encoding a signal sequence which is operably linked to a gene for expression in peanut. With an inducible promoter the rate of transcription increases in response to an inducing agent.

Any inducible promoter can be used in the instant invention. See, Ward, et al., Plant Mol. Biol., 22:361-366 (1993). Exemplary inducible promoters include, but are not limited to, that from the ACEI system which responds to copper (Mett, et al., Proc. Natl. Acad. Sci. USA, 90:4567-4571 (1993)); In2 gene from maize which responds to benzenesulfonamide herbicide safeners (Hershey, et al., Mol. Gen Genetics, 227:229-237 (1991); Gatz, et al., Mol. Gen. Genetics, 243:32-38 (1994)); or Tet repressor from Tn10 (Gatz, et al., Mol. Gen. Genetics, 227:229-237 (1991)). A particularly preferred inducible promoter is a promoter that responds to an inducing agent to which plants do not normally respond. An exemplary inducible promoter is the inducible promoter from a steroid hormone gene, the transcriptional activity of which is induced by a glucocorticosteroid hormone (Schena, et al., Proc. Natl. Acad. Sci. USA, 88:0421 (1991)).

B. Constitutive Promoters—A constitutive promoter is operably linked to a gene for expression in peanut or the constitutive promoter is operably linked to a nucleotide sequence encoding a signal sequence which is operably linked to a gene for expression in peanut.

Many different constitutive promoters can be utilized in the instant invention. Exemplary constitutive promoters include, but are not limited to, the promoters from plant viruses such as the 35S promoter from CaMV (Odell, et al., Nature, 313:810-812 (1985)) and the promoters from such genes as rice actin (McElroy, et al., Plant Cell, 2: 163-171 (1990)); ubiquitin (Christensen, et al., Plant Mol. Biol., 12:619-632 (1989); Christensen, et al., Plant Mol. Biol., 18:675-689 (1992)); pEMU (Last, et al., Theor. Appl. Genet., 81:581-588 (1991)); MAS (Velten, et al., EMBO J., 3:2723-2730 (1984)); and maize H3 histone (Lepetit, et al., Mol. Gen. Genetics, 231: 276-285 (1992); Atanassova, et al., Plant Journal, 2 (3): 291-300 (1992)). The ALS promoter, Xba1/Nco1 fragment 5' to the *Brassica napus* ALS3 structural gene (or a nucleotide sequence similarity to said Xba1/Nco1 fragment), represents a particularly useful constitutive promoter. See, PCT Application WO 96/30530.

C. Tissue-Specific or Tissue-Preferred Promoters—A tissue-specific promoter is operably linked to a gene for expression in peanut. Optionally, the tissue-specific promoter is operably linked to a nucleotide sequence encoding a signal sequence which is operably linked to a gene for expression in peanut. Plants transformed with a gene of interest operably linked to a tissue-specific promoter produce the protein product of the transgene exclusively, or preferentially, in a specific tissue.

Any tissue-specific or tissue-preferred promoter can be utilized in the instant invention. Exemplary tissue-specific or tissue-preferred promoters include, but are not limited to, a root-preferred promoter such as that from the phaseolin gene (Murai, et al., Science, 23:476-482 (1983); Sengupta-Gopalan, et al., Proc. Natl. Acad. Sci. USA, 82:3320-3324 (1985)); a leaf-specific and light-induced promoter such as that from cab or rubisco (Simpson, et al., EMBO J., 4(11): 2723-2729 (1985); Timko, et al., Nature, 318:579-582 (1985)); an anther-specific promoter such as that from LAT52 (Twell, et al., Mol. Gen. Genetics, 217:240-245 (1989)); a pollen-specific promoter such as that from Zm13 (Guerrero, et al., Mol. Gen. Genetics, 244:161-168 (1993)); or a microspore-preferred promoter such as that from apg (Twell, et al., Sex. Plant Reprod., 6:217-224 (1993)).

Signal Sequences for Targeting Proteins to Subcellular Compartments

Transport of a protein produced by transgenes to a subcellular compartment, such as the chloroplast, vacuole, peroxisome, glyoxysome, cell wall, or mitochondrion, or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine during protein synthesis and processing where the encoded protein is ultimately compartmentalized.

The presence of a signal sequence directs a polypeptide to either an intracellular organelle or subcellular compartment or for secretion to the apoplast. Many signal sequences are known in the art. See, for example, Becker, et al., Plant Mol. Biol., 20:49 (1992); Knox, C., et al., Plant Mol. Biol., 9:3-17 (1987); Lerner, et al., Plant Physiol., 91:124-129 (1989); Frontes, et al., Plant Cell, 3:483-496 (1991); Matsuoka, et al., Proc. Natl. Acad. Sci., 88:834 (1991); Gould, et al., J. Cell. Biol., 108:1657 (1989); Creissen, et al., Plant J., 2:129 (1991); Kalderon, et al., Cell, 39:499-509 (1984); Steifel, et al., Plant Cell, 2:785-793 (1990).

Foreign Protein Genes and Agronomic Genes

With transgenic plants according to the present invention, a foreign protein can be produced in commercial quantities. Thus, techniques for the selection and propagation of transformed plants, which are well understood in the art, yield a plurality of transgenic plants which are harvested in a conventional manner, and a foreign protein can then be extracted from a tissue of interest or from total biomass. Protein extraction from plant biomass can be accomplished by known methods which are discussed, for example, by Heney and Orr, Anal. Biochem., 114:92-6 (1981).

According to a preferred embodiment, the transgenic plant provided for commercial production of foreign protein is a peanut plant. In another preferred embodiment, the biomass of interest is seed. For the relatively small number of transgenic plants that show higher levels of expression, a genetic map can be generated, primarily via conventional RFLP, PCR, and SSR analysis, which identifies the approximate chromosomal location of the integrated DNA molecule. For exemplary methodologies in this regard, see, Glick and Thompson, Methods in Plant Molecular Biology and Biotechnology, CRC Press, Inc., Boca Raton, 269:284 (1993). Map information concerning chromosomal location is useful for proprietary protection of a subject transgenic plant.

Wang, et al. discuss "Large Scale Identification, Mapping and Genotyping of Single-Nucleotide Polymorphisms in the Human Genome," Science, 280:1077-1082 (1998), and similar capabilities are becoming increasingly available for the peanut genome. Map information concerning chromosomal location is useful for proprietary protection of a subject transgenic plant. If unauthorized propagation is undertaken and crosses made with other germplasm, the map of the integration region can be compared to similar maps for suspect plants to determine if the latter have a common parentage with the subject plant. Map comparisons would involve hybridizations, RFLP, PCR, SSR, and sequencing, all of which are conventional techniques. SNPs may also be used alone or in combination with other techniques.

Likewise, by means of the present invention, plants can be genetically engineered to express various phenotypes of agronomic interest. Through the transformation of peanut, the expression of genes can be altered to enhance disease resistance, insect resistance, herbicide resistance, agronomic, grain quality, and other traits. Transformation can also be used to insert DNA sequences which control or help control male-sterility. DNA sequences native to peanut, as well as non-native DNA sequences, can be transformed into peanut and used to alter levels of native or non-native proteins. Various promoters, targeting sequences, enhancing sequences, and other DNA sequences can be inserted into the genome for the purpose of altering the expression of proteins. Reduction of the activity of specific genes (also known as gene silencing or gene suppression) is desirable for several aspects of genetic engineering in plants.

Many techniques for gene silencing are well known to one of skill in the art, including, but not limited to, knock-outs (such as by insertion of a transposable element such as mu (Vicki Chandler, The Maize Handbook, Ch. 118 (Springer-Verlag 1994)) or other genetic elements such as a FRT, Lox, or other site specific integration site, antisense technology (see, e.g., Sheehy, et al., PNAS USA, 85:8805-8809 (1988); and U.S. Pat. Nos. 5,107,065, 5,453,566, and 5,759,829); co-suppression (e.g., Taylor, Plant Cell, 9:1245 (1997); Jorgensen, Trends Biotech., 8(12):340-344 (1990); Flavell, PNAS USA, 91:3490-3496 (1994); Finnegan, et al., Bio/Technology, 12:883-888 (1994); Neuhuber, et al., Mol. Gen. Genet., 244:230-241 (1994)); RNA interference (Napoli, et al., Plant Cell, 2:279-289 (1990); U.S. Pat. No. 5,034,323; Sharp, Genes Dev., 13:139-141 (1999); Zamore, et al., Cell, 101:25-33 (2000); Montgomery, et al., PNAS USA, 95:15502-15507 (1998)), virus-induced gene silencing (Burton, et al., Plant Cell, 12:691-705 (2000); Baulcombe, Curr. Op. Plant Bio., 2:109-113 (1999)); target-RNA-specific ribozymes (Haseloff, et al., Nature, 334: 585-591 (1988)); hairpin structures (Smith, et al., Nature, 407:319-320 (2000); WO 99/53050; WO 98/53083); MicroRNA (Aukerman & Sakai, Plant Cell, 15:2730-2741 (2003)); ribozymes (Steinecke, et al., EMBO J., 11:1525 (1992); Perriman, et al., Antisense Res. Dev., 3:253 (1993)); oligonucleotide mediated targeted modification (e.g., WO 03/076574 and WO 99/25853); Zn-finger targeted molecules (e.g., WO 01/52620, WO 03/048345, and WO 00/42219); and other methods or combinations of the above methods known to those of skill in the art.

Likewise, by means of the present invention, agronomic genes can be expressed in transformed plants. More particularly, plants can be genetically engineered to express various phenotypes of agronomic interest. Exemplary genes implicated in this regard include, but are not limited to, those categorized below:

1. Genes that Confer Resistance to Pests or Disease and that Encode:

A. Plant disease resistance genes. Plant defenses are often activated by specific interaction between the product of a disease resistance gene (R) in the plant and the product of a corresponding avirulence (Avr) gene in the pathogen. A plant variety can be transformed with one or more cloned resistance genes to engineer plants that are resistant to specific pathogen strains. See, for example, Jones, et al., Science, 266:789 (1994) (cloning of the tomato Cf-9 gene for resistance to *Cladosporium fulvum*); Martin, et al., Science, 262:1432 (1993) (tomato Pto gene for resistance to *Pseudomonas syringae* pv. tomato encodes a protein kinase); Mindrinos, et al., Cell, 78:1089 (1994) (Arabidopsis RSP2 gene for resistance to *Pseudomonas syringae*); McDowell & Woffenden, Trends Biotechnol., 21(4):178-83 (2003); and Toyoda, et al., Transgenic Res., 11 (6):567-82 (2002).

B. A gene conferring resistance to a pest, such as soybean cyst nematode. See, e.g., PCT Application WO 96/30517 and PCT Application WO 93/19181.

C. A *Bacillus thuringiensis* protein, a derivative thereof or a synthetic polypeptide modeled thereon. See, for example, Geiser, et al., Gene, 48:109 (1986), who disclose the cloning and nucleotide sequence of a Bt δ-endotoxin gene. Moreover, DNA molecules encoding δ-endotoxin genes can be purchased from American Type Culture Collection, Manassas, Va., for example, under ATCC Accession Nos. 40098, 67136, 31995, and 31998.

D. A lectin. See, for example, Van Damme, et al., Plant Molec. Biol., 24:25 (1994), who disclose the nucleotide sequences of several *Clivia miniata* mannose-binding lectin genes.

E. A vitamin-binding protein such as avidin. See, PCT Application US 93/06487, which teaches the use of avidin and avidin homologues as larvicides against insect pests.

F. An enzyme inhibitor, for example, a protease or proteinase inhibitor or an amylase inhibitor. See, for example, Abe, et al., J. Biol. Chem., 262:16793 (1987) (nucleotide sequence of rice cysteine proteinase inhibitor); Huub, et al., Plant Molec. Biol., 21:985 (1993) (nucleotide sequence of cDNA encoding tobacco proteinase inhibitor I); Sumitani, et al., Biosci. Biotech. Biochem., 57:1243 (1993) (nucleotide sequence of *Streptomyces nitrosporeus* α-amylase inhibitor); and U.S. Pat. No. 5,494,813 (Hepher and Atkinson, issued Feb. 27, 1996).

G. An insect-specific hormone or pheromone, such as an ecdysteroid or juvenile hormone, a variant thereof, a mimetic based thereon, or an antagonist or agonist thereof. See, for example, the disclosure by Hammock, et al., Nature, 344:458 (1990), of baculovirus expression of cloned juvenile hormone esterase, an inactivator of juvenile hormone.

H. An insect-specific peptide or neuropeptide which, upon expression, disrupts the physiology of the affected pest. For example, see the disclosures of Regan, J. Biol. Chem., 269:9 (1994) (expression cloning yields DNA coding for insect diuretic hormone receptor); Pratt, et al., Biochem. Biophys. Res. Comm., 163:1243 (1989) (an allostatin is identified in *Diploptera puntata*); Chattopadhyay, et al., Critical Reviews in Microbiology, 30(1):33-54 (2004); Zjawiony, J Nat Prod, 67(2):300-310 (2004); Carlini & Grossi-de-Sa, Toxicon, 40(11):1515-1539 (2002); Ussuf, et al., Curr Sci., 80(7):847-853 (2001); Vasconcelos & Oliveira, Toxicon, 44(4):385-403 (2004). See also, U.S. Pat. No. 5,266,317 to Tomalski, et al., which discloses genes encoding insect-specific, paralytic neurotoxins.

I. An insect-specific venom produced in nature by a snake, a wasp, etc. For example, see, Pang, et al., Gene, 116:165 (1992), for disclosure of heterologous expression in plants of a gene coding for a scorpion insectotoxic peptide.

J. An enzyme responsible for a hyperaccumulation of a monoterpene, a sesquiterpene, a steroid, hydroxamic acid, a phenylpropanoid derivative, or another non-protein molecule with insecticidal activity.

K. An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase, and a glucanase, whether natural or synthetic. See, PCT Application WO 93/02197 (Scott, et al.), which discloses the nucleotide sequence of a callase gene. DNA molecules which contain chitinase-encoding sequences can be obtained, for example, from the ATCC under Accession Nos. 39637 and 67152. See also, Kramer, et al., Insect Biochem. Molec. Biol., 23:691 (1993), who teach the nucleotide sequence of a cDNA encoding tobacco hornworm chitinase, and Kawalleck, et al., Plant Molec. Biol., 21:673 (1993), who provide the nucleotide sequence of the parsley ubi4-2 polyubiquitin gene, U.S. Pat. Nos. 7,145,060, 7,087,810, and 6,563,020.

L. A molecule that stimulates signal transduction. For example, see the disclosure by Botella, et al., Plant Molec. Biol., 24:757 (1994), of nucleotide sequences for mung bean calmodulin cDNA clones, and Griess, et al., Plant Physiol., 104:1467 (1994), who provide the nucleotide sequence of a maize calmodulin cDNA clone.

M. A hydrophobic moment peptide. See, PCT Application WO 95/16776 and U.S. Pat. No. 5,580,852, which disclose peptide derivatives of tachyplesin which inhibit fungal plant pathogens, and PCT Application WO 95/18855 and U.S. Pat. No. 5,607,914 which teaches synthetic antimicrobial peptides that confer disease resistance.

N. A membrane permease, a channel former or a channel blocker. For example, see the disclosure of Jaynes, et al., Plant Sci, 89:43 (1993), of heterologous expression of a cecropin-β lytic peptide analog to render transgenic tobacco plants resistant to *Pseudomonas solanacearum*.

O. A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See, Beachy, et al., Ann. Rev. Phytopathol., 28:451 (1990). Coat protein-mediated resistance has been conferred upon transformed plants against alfalfa mosaic virus, cucumber mosaic virus, and tobacco mosaic virus.

P. An insect-specific antibody or an immunotoxin derived therefrom. Thus, an antibody targeted to a critical metabolic function in the insect gut would inactivate an affected enzyme, killing the insect. See, Taylor, et al., Abstract #497, Seventh Int'l Symposium on Molecular Plant-Microbe Interactions (Edinburgh, Scotland 1994) (enzymatic inactivation in transgenic tobacco via production of single-chain antibody fragments).

Q. A virus-specific antibody. See, for example, Tavladoraki, et al., Nature, 366:469 (1993), who show that transgenic plants expressing recombinant antibody genes are protected from virus attack.

R. A developmental-arrestive protein produced in nature by a pathogen or a parasite. Thus, fungal endo-α-1,4-D-polygalacturonases facilitate fungal colonization and plant nutrient release by solubilizing plant cell wall homo-α-1,4-D-galacturonase. See, Lamb, et al., Bio/Technology, 10:1436 (1992). The cloning and characterization of a gene which encodes a bean endopolygalacturonase-inhibiting protein is described by Toubart, et al., Plant J., 2:367 (1992).

S. A developmental-arrestive protein produced in nature by a plant. For example, Logemann, et al., Bio/Technology, 10:305 (1992), have shown that transgenic plants expressing the barley ribosome-inactivating gene have an increased resistance to fungal disease.

T. Genes involved in the Systemic Acquired Resistance (SAR) Response and/or the pathogenesis-related genes. Briggs, S., Current Biology, 5(2) (1995); Pieterse & Van Loon, Curr. Opin. Plant Bio., 7(4):456-64 (2004); and Somssich, Cell, 113(7):815-6 (2003).

U. Antifungal genes. See, Cornelissen and Melchers, Plant Physiol., 101:709-712 (1993); Parijs, et al., Planta, 183:258-264 (1991); and Bushnell, et al., Can. J. of Plant Path., 20(2): 137-149 (1998). See also, U.S. Pat. No. 6,875,907.

V. Detoxification genes, such as for fumonisin, beauvericin, moniliformin, and zearalenone and their structurally-related derivatives. See, for example, U.S. Pat. No. 5,792,931.

W. Cystatin and cysteine proteinase inhibitors. See, U.S. Pat. No. 7,205,453.

X. Defensin genes. See, WO 03/000863 and U.S. Pat. No. 6,911,577.

Y. Genes conferring resistance to nematodes, such as root knot nematode and root lesion nematode. See, e.g., PCT Applications WO 96/30517, WO 93/19181, and WO 03/033651; Urwin, et al., Planta, 204:472-479 (1998); Williamson, Curr Opin Plant Bio., 2(4):327-31 (1999).

Z. Genes that confer resistance to *Phytophthora* Root Rot, such as the Rps 1, Rps 1-a, Rps 1-b, Rps 1-c, Rps 1-d, Rps 1-e, Rps 1-k, Rps 2, Rps 3-a, Rps 3-b, Rps 3-c, Rps 4, Rps 5, Rps 6, Rps 7, and other Rps genes. See, for example, Shoemaker, et al., *Phytophthora* Root Rot Resistance Gene Mapping in Soybean, Plant Genome IV Conference, San Diego, Calif. (1995).

AA. Genes that confer resistance to Brown Stem Rot, such as described in U.S. Pat. No. 5,689,035 and incorporated by reference for this purpose.

Any of the above-listed disease or pest resistance genes (A-AA) can be introduced into the claimed peanut cultivar through a variety of means including, but not limited to, transformation and crossing.

2. Genes that Confer Resistance to an Herbicide, for Example:

A. An herbicide that inhibits the growing point or meristem, such as an imidazolinone or a sulfonylurea. Exemplary genes in this category code for mutant ALS and AHAS enzyme as described, for example, by Lee, et al., *EMBO J.*, 7:1241 (1988) and Miki, et al., *Theor. Appl. Genet.*, 80:449 (1990), respectively.

B. Glyphosate (resistance conferred by mutant 5-enolpyruvlshikimate-3-phosphate synthase (EPSPS) and aroA genes, respectively) and other phosphono compounds, such as glufosinate (phosphinothricin acetyl transferase (PAT) and *Streptomyces hygroscopicus* PAT bar genes), pyridinoxy or phenoxy proprionic acids, and cyclohexanediones (ACCase inhibitor-encoding genes). See, for example, U.S. Pat. No. 4,940,835 to Shah, et al., which discloses the nucleotide sequence of a form of EPSPS which can confer glyphosate resistance. U.S. Pat. No. 5,627,061 to Barry, et al., also describes genes encoding EPSPS enzymes. See also, U.S. Pat. Nos. 6,566,587, 6,338,961, 6,248,876, 6,040,497, 5,804,425, 5,633,435, 5,145,783, 4,971,908, 5,312,910, 5,188,642, 4,940,835, 5,866,775, 6,225,114, 6,130,366, 5,310,667, 4,535,060, 4,769,061, 5,633,448, 5,510,471, RE 36,449, RE 37,287, and 5,491,288; and International Publications EP1173580, WO 01/66704, EP1173581, and EP1173582, which are incorporated herein by reference for this purpose. Glyphosate resistance is also imparted to plants that express a gene that encodes a glyphosate oxido-reductase enzyme, as described more fully in U.S. Pat. Nos. 5,776,760 and 5,463,175, which are incorporated herein by reference for this purpose. In addition, glyphosate resistance can be imparted to plants by the over expression of genes encoding glyphosate N-acetyltransferase. See, for example, U.S. Pat. No. 7,462,481. A DNA molecule encoding a mutant aroA gene can be obtained under ATCC Accession No. 39256, and the nucleotide sequence of the mutant gene is disclosed in U.S. Pat. No. 4,769,061 to Comai. European Patent Appl. No. 0 333 033 to Kumada, et al. and U.S. Pat. No. 4,975,374 to Goodman, et al., disclose nucleotide sequences of glutamine synthetase genes which confer resistance to herbicides such as L-phosphinothricin. The nucleotide sequence of a PAT gene is provided in European Patent Appl. No. 0 242 246 to Leemans, et al. DeGreef, et al., *Bio/Technology*, 7:61 (1989) describe the production of transgenic plants that express chimeric bar genes coding for phosphinothricin acetyl transferase activity. Exemplary of genes conferring resistance to phenoxy proprionic acids and cyclohexones, such as sethoxydim and haloxyfop are the Acc1-S1, Acc1-S2, and Acc2-S3 genes described by Marshall, et al., *Theor. Appl. Genet.*, 83:435 (1992).

C. An herbicide that inhibits photosynthesis, such as a triazine (psbA and gs+ genes) and a benzonitrile (nitrilase gene). Przibila, et al., *Plant Cell*, 3:169 (1991), describe the transformation of *Chlamydomonas* with plasmids encoding mutant psbA genes. Nucleotide sequences for nitrilase genes are disclosed in U.S. Pat. No. 4,810,648 to Stalker and DNA molecules containing these genes are available under ATCC Accession Nos. 53435, 67441, and 67442. Cloning and expression of DNA coding for a glutathione S-transferase is described by Hayes, et al., *Biochem. J.*, 285:173 (1992).

D. Acetohydroxy acid synthase, which has been found to make plants that express this enzyme resistant to multiple types of herbicides, has been introduced into a variety of plants. See, Hattori, et al., *Mol. Gen. Genet.*, 246:419 (1995). Other genes that confer tolerance to herbicides include a gene encoding a chimeric protein of rat cytochrome P4507A1 and yeast NADPH-cytochrome P450 oxidoreductase (Shiota, et al., *Plant Physiol.*, 106:17 (1994)); genes for glutathione reductase and superoxide dismutase (Aono, et al., *Plant Cell Physiol.*, 36:1687 (1995)); and genes for various phosphotransferases (Datta, et al., *Plant Mol. Biol.*, 20:619 (1992)).

E. Protoporphyrinogen oxidase (protox) is necessary for the production of chlorophyll, which is necessary for all plant survival. The protox enzyme serves as the target for a variety of herbicidal compounds. These herbicides also inhibit growth of all the different species of plants present, causing their total destruction. The development of plants containing altered protox activity which are resistant to these herbicides are described in U.S. Pat. Nos. 6,288,306, 6,282,837, 5,767,373, and International Publication WO 01/12825.

Any of the above listed herbicide genes (A-E) can be introduced into the claimed peanut cultivar through a variety of means including but not limited to transformation and crossing.

3. Genes that Confer or Contribute to a Value-Added Trait, Such as:

A. Modified fatty acid metabolism, for example, by transforming a plant with an antisense gene of stearyl-ACP desaturase to increase stearic acid content of the plant. See, Knultzon, et al., *Proc. Natl. Acad. Sci. USA*, 89:2625 (1992).

B. Decreased phytate content: 1) Introduction of a phytase-encoding gene enhances breakdown of phytate, adding more free phosphate to the transformed plant. For example, see, Van Hartingsveldt, et al., *Gene*, 127:87 (1993), for a disclosure of the nucleotide sequence of an *Aspergillus niger* phytase gene. 2) Up-regulation of a gene that reduces phytate content. In maize, this, for example, could be accomplished by cloning and then re-introducing DNA associated with one or more of the alleles, such as the LPA alleles, identified in maize mutants characterized by low levels of phytic acid, such as in Raboy, et al., *Maydica*, 35:383 (1990), and/or by altering inositol kinase activity as in WO 02/059324, U.S. Publ. No. 2003/000901, WO 03/027243, U.S. Publ. No. 2003/0079247, WO 99/05298, U.S. Pat. No. 6,197,561, U.S. Pat. No. 6,291,224, U.S. Pat. No. 6,391,348, WO 2002/059324, U.S. Publ. No. 2003/0079247, WO 98/45448, W 099/55882, and WO 01/04147.

C. Modified carbohydrate composition effected, for example, by transforming plants with a gene coding for an enzyme that alters the branching pattern of starch, or a gene altering thioredoxin, such as NTR and/or TRX (see, U.S. Pat. No. 6,531,648, which is incorporated by reference for this purpose), and/or a gamma zein knock out or mutant, such as cs27 or TUSC27 or en27 (see, U.S. Pat. No. 6,858,778, and U.S. Publ. Nos. 2005/0160488 and 2005/0204418, which are incorporated by reference for this purpose). See, Shiroza, et al., *J. Bacteriol.*, 170:810 (1988) (nucleotide sequence of *Streptococcus mutans* fructosyltransferase gene); Steinmetz, et al., *Mol. Gen. Genet.*, 200:220 (1985) (nucleotide sequence of *Bacillus subtilis* levansucrase gene); Pen, et al., *Bio/Technology*, 10:292 (1992) (production of transgenic plants that express *Bacillus licheniformis* alpha-amylase); Elliot, et al., *Plant Molec. Biol.*, 21:515 (1993) (nucleotide sequences of tomato invertase genes); Sogaard, et al., *J. Biol. Chem.*, 268: 22480 (1993) (site-directed mutagenesis of barley alpha-amylase gene); Fisher, et al., *Plant Physiol.*, 102:1045 (1993) (maize endosperm starch branching enzyme II); WO 99/10498 (improved digestibility and/or starch extraction through modification of UDP-D-xylose 4-epimerase, Fragile 1 and 2, Ref 1, HCHL, C4H); U.S. Pat. No. 6,232,529 (method of producing high oil seed by modification of starch levels (AGP)). The fatty acid modification genes mentioned above may also be used to affect starch content and/or composition through the interrelationship of the starch and oil pathways.

D. Elevated oleic acid via FAD-2 gene modification and/or decreased linolenic acid via FAD-3 gene modification. See, U.S. Pat. Nos. 6,063,947, 6,323,392, and International Publication WO 93/11245. Although as many as 12 fatty acids have been reported in peanuts, only 3 are present in amounts exceeding 5%: palmitic, oleic and linoleic (Ahmed, E. M. et al in *Peanut Science and Technology* (1982 H. E. Pattec, et al., ed)). These three fatty acids comprise about 90% of the fatty acid composition of the oil, with oleic and linoleic comprising about 80%. The remainder of the fatty acids comprise about 10%, each ranging in concentration from 0.02% to 2.59%. The American Heart Association and the American Health Foundation have recommended diet modifications to achieve lower serum cholesterol levels in the population. These diet modifications include reducing consumption of saturated fatty acids and thereby increasing the polyunsaturated to saturated (P/S) ratio in the diet (Technical Committee, *Food Fats and Oils*, $5^{th}$ ed. (1992)). Edible peanut oils with a higher percentage of unsaturated fatty acids are desired for these cardio-vascular health reasons (Mattson, F. H. et al., *J Lipid Research* 26:194-202 (1985)).

E. Altering conjugated linolenic or linoleic acid content, such as in WO 01/12800. Altering LEC1, AGP, Dek1, Superal1, mi1ps, and various Ipa genes, such as Ipa1, Ipa3, hpt, or hggt. See, for example, WO 02/42424, WO 98/22604, WO 03/011015, WO 02/057439, WO 03/011015, U.S. Pat. Nos. 6,423,886, 6,197,561, 6,825,397, 7,157,621, U.S. Publ. No. 2003/0079247, and Rivera-Madrid, R., et al., *Proc. Natl. Acad. Sci.*, 92:5620-5624 (1995).

F. Altered antioxidant content or composition, such as alteration of tocopherol or tocotrienols. See, for example, U.S. Pat. Nos. 6,787,683, 7,154,029, WO 00/68393 (involving the manipulation of antioxidant levels through alteration of a phytl prenyl transferase (ppt)); WO 03/082899 (through alteration of a homogentisate geranyl geranyl transferase (hggt)).

G. Altered essential seed amino acids. See, for example, U.S. Pat. No. 6,127,600 (method of increasing accumulation of essential amino acids in seeds); U.S. Pat. No. 6,080,913 (binary methods of increasing accumulation of essential amino acids in seeds); U.S. Pat. No. 5,990,389 (high lysine); U.S. Pat. No. 5,850,016 (alteration of amino acid compositions in seeds); U.S. Pat. No. 5,885,802 (high methionine); U.S. Pat. No. 5,885,801 (high threonine); U.S. Pat. No. 6,664, 445 (plant amino acid biosynthetic enzymes); U.S. Pat. No. 6,459,019 (increased lysine and threonine); U.S. Pat. No. 6,441,274 (plant tryptophan synthase beta subunit); U.S. Pat. No. 6,346,403 (methionine metabolic enzymes); U.S. Pat. No. 5,939,599 (high sulfur); U.S. Pat. No. 5,912,414 (increased methionine); U.S. Pat. No. 5,633,436 (increasing sulfur amino acid content); U.S. Pat. No. 5,559,223 (synthetic storage proteins with defined structure containing programmable levels of essential amino acids for improvement of the nutritional value of plants); U.S. Pat. No. 6,194,638 (hemicellulose); U.S. Pat. No. 7,098,381 (UDPGdH); U.S. Pat. No. 6,194,638 (RGP); U.S. Pat. Nos. 6,399,859, 6,930,225, 7,179,955, and 6,803,498; U.S. Publ. No. 2004/0068767; WO 99/40209 (alteration of amino acid compositions in seeds); WO 99/29882 (methods for altering amino acid content of proteins); WO 98/20133 (proteins with enhanced levels of essential amino acids); WO 98/56935 (plant amino acid biosynthetic enzymes); WO 98/45458 (engineered seed protein having higher percentage of essential amino acids); WO 98/42831 (increased lysine); WO 96/01905 (increased threonine); WO 95/15392 (increased lysine); WO 01/79516; and WO 00/09706 (Ces A: cellulose synthase).

4. Genes that Control Male Sterility:

There are several methods of conferring genetic male sterility available, such as multiple mutant genes at separate locations within the genome that confer male sterility, as disclosed in U.S. Pat. Nos. 4,654,465 and 4,727,219 to Brar, et al., and chromosomal translocations as described by Patterson in U.S. Pat. Nos. 3,861,709 and 3,710,511. In addition to these methods, Albertsen, et al., U.S. Pat. No. 5,432,068, describes a system of nuclear male sterility which includes: identifying a gene which is critical to male fertility; silencing this native gene which is critical to male fertility; removing the native promoter from the essential male fertility gene and replacing it with an inducible promoter; inserting this genetically engineered gene back into the plant; and thus creating a plant that is male sterile because the inducible promoter is not "on" resulting in the male fertility gene not being transcribed. Fertility is restored by inducing, or turning "on," the promoter, which in turn allows the gene that confers male fertility to be transcribed.

A. Introduction of a deacetylase gene under the control of a tapetum-specific promoter and with the application of the chemical N-Ac-PPT. See, International Publication WO 01/29237.

B. Introduction of various stamen-specific promoters. See, International Publications WO 92/13956 and WO 92/13957.

C. Introduction of the barnase and the barstar genes. See, Paul, et al., Plant Mol. Biol., 19:611-622 (1992).

For additional examples of nuclear male and female sterility systems and genes, see also, U.S. Pat. Nos. 5,859,341, 6,297,426, 5,478,369, 5,824,524, 5,850,014, and 6,265,640, all of which are hereby incorporated by reference.

5. Genes that Create a Site for Site Specific DNA Integration:

This includes the introduction of FRT sites that may be used in the FLP/FRT system and/or Lox sites that may be used in the Cre/Loxp system. See, for example, Lyznik, et al., Site-Specific Recombination for Genetic Engineering in Plants, *Plant Cell Rep*, 21:925-932 (2003) and WO 99/25821, which are hereby incorporated by reference. Other systems that may be used include the Gin recombinase of phage Mu (Maeser, et al. (1991); Vicki Chandler, The Maize Handbook, Ch. 118 (Springer-Verlag 1994)); the Pin recombinase of *E. coli* (Enomoto, et al. (1983)); and the R/RS system of the pSR1 plasmid (Araki, et al. (1992)).

6. Genes that Affect Abiotic Stress Resistance:

Genes that affect abiotic stress resistance (including but not limited to flowering, pod and seed development, enhancement of nitrogen utilization efficiency, altered nitrogen responsiveness, drought resistance or tolerance, cold resistance or tolerance, and salt resistance or tolerance) and increased yield under stress. For example, see: WO 00/73475 where water use efficiency is altered through alteration of malate; U.S. Pat. Nos. 5,892,009, 5,965,705, 5,929,305, 5,891,859, 6,417,428, 6,664,446, 6,706,866, 6,717,034, 6,801,104, WO 2000/060089, WO 2001/026459, WO 2001/035725, WO 2001/034726, WO 2001/035727, WO 2001/036444, WO 2001/036597, WO 2001/036598, WO 2002/015675, WO 2002/017430, WO 2002/077185, WO 2002/079403, WO 2003/013227, WO 2003/013228, WO 2003/014327, WO 2004/031349, WO 2004/076638, WO 98/09521, and WO 99/38977 describing genes, including CBF genes and transcription factors effective in mitigating the negative effects of freezing, high salinity, and drought on plants, as well as conferring other positive effects on plant phenotype; U.S. Publ. No. 2004/0148654 and WO 01/36596, where abscisic acid is altered in plants resulting in improved plant phenotype, such as increased yield and/or increased tolerance to abiotic stress; WO 2000/006341, WO 04/090143, U.S. Pat. No. 7,531,723, and U.S. Pat. No. 6,992,237, where cytokinin expression is modified resulting in plants with increased stress tolerance, such as drought tolerance, and/or increased yield. See also, WO 02/02776, WO 2003/052063, JP 2002281975, U.S. Pat. No. 6,084,153, WO 01/64898, and U.S. Pat. Nos. 6,177,275 and 6,107,547 (enhancement of nitrogen utilization and altered nitrogen responsiveness). For ethylene alteration, see, U.S. Publ. Nos. 2004/0128719, 2003/0166197, and WO 2000/32761. For plant transcription factors or transcriptional regulators of abiotic stress, see, e.g., U.S. Publ. Nos. 2004/0098764 or 2004/0078852.

Other genes and transcription factors that affect plant growth and agronomic traits, such as yield, flowering, plant growth, and/or plant structure, can be introduced or introgressed into plants. See, e.g., WO 97/49811 (LHY), WO 98/56918 (ESD4), WO 97/10339, U.S. Pat. Nos. 6,573,430 (TFL), 6,713,663 (FT), 6,794,560, 6,307,126 (GAI), WO 96/14414 (CON), WO 96/38560, WO 01/21822 (VRN1), WO 00/44918 (VRN2), WO 99/49064 (GI), WO 00/46358 (FR1), WO 97/29123, WO 99/09174 (D8 and Rht), WO 2004/076638, and WO 004/031349 (transcription factors).

Methods for Peanut Transformation

Numerous methods for plant transformation have been developed including biological and physical plant transformation protocols. See, for example, Miki, et al., "Procedures for Introducing Foreign DNA into Plants," in *Methods in Plant Molecular Biology and Biotechnology*, Glick and Thompson Eds., CRC Press, Inc., Boca Raton, pp. 67-88 (1993). In addition, expression vectors and in-vitro culture methods for plant cell or tissue transformation and regeneration of plants are available. See, for example, Gruber, et al., "Vectors for Plant Transformation," in *Methods in Plant Molecular Biology and Biotechnology*, Glick and Thompson Eds., CRC Press, Inc., Boca Raton, pp. 89-119 (1993).

A. *Agrobacterium*-mediated Transformation—One method for introducing an expression vector into plants is based on the natural transformation system of *Agrobacterium*. See, for example, Horsch, et al., *Science*, 227:1229 (1985). *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. See, for example, Kado, C. I., *Crit. Rev. Plant Sci.*, 10:1 (1991). Descriptions of *Agrobacterium* vector systems and methods for *Agrobacterium*-mediated gene transfer are provided by Gruber, et al., supra, Miki, et al., supra, and Moloney, et al., *Plant Cell Reports*, 8:238 (1989). See also, U.S. Pat. No. 5,563,055 (Townsend and Thomas), issued Oct. 8, 1996.

B. Direct Gene Transfer—Several methods of plant transformation, collectively referred to as direct gene transfer, have been developed as an alternative to *Agrobacterium*-mediated transformation. A generally applicable method of plant transformation is microprojectile-mediated transformation where DNA is carried on the surface of microprojectiles measuring 1 to 4 µm. The expression vector is introduced into plant tissues with a biolistic device that accelerates the microprojectiles to speeds of 300 to 600 m/s which is sufficient to penetrate plant cell walls and membranes. Sanford, et al., *Part. Sci. Technol.*, 5:27 (1987); Sanford, J. C., *Trends Biotech.*, 6:299 (1988); Klein, et al., *Bio/Tech.*, 6:559-563 (1988); Sanford, J. C., *Physiol Plant*, 7:206 (1990); Klein, et al., *Biotechnology*, 10:268 (1992). See also, U.S. Pat. No. 5,015,580 (Christou, et al.), issued May 14, 1991 and U.S. Pat. No. 5,322,783 (Tomes, et al.), issued Jun. 21, 1994.

Another method for physical delivery of DNA to plants is sonication of target cells. Zhang, et al., *Bio/Technology*, 9:996 (1991). Alternatively, liposome and spheroplast fusion have been used to introduce expression vectors into plants. Deshayes, et al., *EMBO J.*, 4:2731 (1985); Christou, et al., *Proc Natl. Acad. Sci. USA*, 84:3962 (1987). Direct uptake of DNA into protoplasts using $CaCl_2$ precipitation, polyvinyl alcohol or poly-L-ornithine have also been reported. Hain, et al., *Mol. Gen. Genet.*, 199:161 (1985) and Draper, et al., *Plant Cell Physiol.*, 23:451 (1982). Electroporation of protoplasts and whole cells and tissues have also been described (Donn, et al., In Abstracts of VIIth International Congress on Plant Cell and Tissue Culture IAPTC, A2-38, p. 53 (1990); D'Halluin, et al., *Plant Cell*, 4:1495-1505 (1992); and Spencer, et al., *Plant Mol. Biol.*, 24:51-61 (1994)).

Following transformation of peanut target tissues, expression of the above-described selectable marker genes allows for preferential selection of transformed cells, tissues, and/or plants, using regeneration and selection methods well known in the art.

The foregoing methods for transformation would typically be used for producing a transgenic variety. The transgenic variety could then be crossed with another (non-transformed or transformed) variety in order to produce a new transgenic variety. Alternatively, a genetic trait that has been engineered into a particular peanut line using the foregoing transformation techniques could be moved into another line using traditional backcrossing techniques that are well known in the plant breeding arts. For example, a backcrossing approach could be used to move an engineered trait from a public, non-elite variety into an elite variety, or from a variety containing a foreign gene in its genome into a variety or varieties that do not contain that gene. As used herein, "crossing" can refer to a simple x by y cross or the process of backcrossing depending on the context.

Genetic Marker Profile Through SSR and First Generation Progeny

In addition to phenotypic observations, a plant can also be identified by its genotype. The genotype of a plant can be characterized through a genetic marker profile which can identify plants of the same variety, or a related variety, or be used to determine or validate a pedigree. Genetic marker profiles can be obtained by techniques such as Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs) (which are also referred to as Microsatellites), and Single Nucleotide Polymorphisms (SNPs). For example, see, Cregan, et al., "An Integrated Genetic Linkage Map of the Soybean Genome," *Crop Science,* 39:1464-1490 (1999) and Berry, et al., "Assessing Probability of Ancestry Using Simple Sequence Repeat Profiles: Applications to Maize Inbred Lines and Soybean Varieties," *Genetics,* 165:331-342 (2003), each of which are incorporated by reference herein in their entirety. Particular markers used for these purposes are not limited to any particular set of markers, but are envisioned to include any type of marker and marker profile which provides a means of distinguishing varieties. One method of comparison is to use only homozygous loci for peanut cultivar UFT113.

Primers and PCR protocols for assaying these and other markers may be used for identification of peanut cultivar UFT113, and plant parts and plant cells of peanut cultivar UFT113, the genetic profile may be used to identify a peanut plant produced through the use of peanut cultivar UFT113 or to verify a pedigree for progeny plants produced through the use of peanut cultivar UFT113. The genetic marker profile is also useful in breeding and developing backcross conversions.

The present invention comprises a peanut plant characterized by molecular and physiological data obtained from the representative sample of said variety deposited with the American Type Culture Collection (ATCC). Further provided by the invention is a peanut plant formed by the combination of the disclosed peanut plant or plant cell with another peanut plant or cell and comprising the homozygous alleles of the variety.

Means of performing genetic marker profiles using SSR polymorphisms are well known in the art. SSRs are genetic markers based on polymorphisms in repeated nucleotide sequences, such as microsatellites. A marker system based on SSRs can be highly informative in linkage analysis relative to other marker systems in that multiple alleles may be present. Another advantage of this type of marker is that, through use of flanking primers, detection of SSRs can be achieved, for example, by the polymerase chain reaction (PCR), thereby eliminating the need for labor-intensive Southern hybridization. The PCR detection is done by use of two oligonucleotide primers flanking the polymorphic segment of repetitive DNA. Repeated cycles of heat denaturation of the DNA followed by annealing of the primers to their complementary sequences at low temperatures, and extension of the annealed primers with DNA polymerase, comprise the major part of the methodology.

Following amplification, markers can be scored by electrophoresis of the amplification products. Scoring of marker genotype is based on the size of the amplified fragment, which may be measured by the number of base pairs of the fragment. While variation in the primer used or in laboratory procedures can affect the reported fragment size, relative values should remain constant regardless of the specific primer or laboratory used. When comparing varieties it is preferable if all SSR profiles are performed in the same lab.

The SSR profile of peanut plant UFT113 can be used to identify plants comprising peanut cultivar UFT113 as a parent, since such plants will comprise the same homozygous alleles as peanut cultivar UFT113. Because the peanut variety is essentially homozygous at all relevant loci, most loci should have only one type of allele present. In contrast, a genetic marker profile of an $F_1$ progeny should be the sum of those parents, e.g., if one parent was homozygous for allele x at a particular locus, and the other parent homozygous for allele y at that locus, then the $F_1$ progeny will be xy (heterozygous) at that locus. Subsequent generations of progeny produced by selection and breeding are expected to be of genotype x (homozygous), y (homozygous), or xy (heterozygous) for that locus position. When the $F_1$ plant is selfed or sibbed for successive filial generations, the locus should be either x or y for that position.

In addition, plants and plant parts substantially benefiting from the use of peanut cultivar UFT113 in their development, such as peanut cultivar UFT113 comprising a backcross conversion, transgene, or genetic sterility factor, may be identified by having a molecular marker profile with a high percent identity to peanut cultivar UFT113. Such a percent identity might be 95%, 96%, 97%, 98%, 99%, 99.5%, or 99.9% identical to peanut cultivar UFT113.

The SSR profile of peanut cultivar UFT113 can also be used to identify essentially derived varieties and other progeny varieties developed from the use of peanut cultivar UFT113, as well as cells and other plant parts thereof. Progeny plants and plant parts produced using peanut cultivar UFT113 may be identified by having a molecular marker profile of at least 25%, 30%, 35%, 40%, 45%, 50%, 55%, 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 99.5% genetic contribution from peanut variety, as measured by either percent identity or percent similarity. Such progeny may be further characterized as being within a pedigree distance of peanut cultivar UFT113, such as within 1, 2, 3, 4, or 5 or less cross-pollinations to a peanut plant other than peanut cultivar UFT113 or a plant that has peanut cultivar UFT113 as a progenitor. Unique molecular profiles may be identified with other molecular tools such as SNPs and RFLPs.

While determining the SSR genetic marker profile of the plants described supra, several unique SSR profiles may also be identified which did not appear in either parent of such plant. Such unique SSR profiles may arise during the breeding process from recombination or mutation. A combination of several unique alleles provides a means of identifying a plant variety, an $F_1$ progeny produced from such variety, and progeny produced from such variety.

Single-Gene Conversions

When the term "peanut plant" is used in the context of the present invention, this also includes any single gene conversions of that variety. The term single gene converted plant as used herein refers to those peanut plants which are developed by a plant breeding technique called backcrossing wherein essentially all of the desired morphological and physiological characteristics of a variety are recovered in addition to the single gene transferred into the variety via the backcrossing technique. Backcrossing methods can be used with the present invention to improve or introduce a characteristic into the variety. The term "backcrossing" as used herein refers to the repeated crossing of a hybrid progeny back to the recurrent parent, i.e., backcrossing 1, 2, 3, 4, 5, 6, 7, 8, or more times to the recurrent parent. The parental peanut plant that contributes the gene for the desired characteristic is termed the nonrecurrent or donor parent. This terminology refers to the fact that the nonrecurrent parent is used one time in the backcross protocol and therefore does not recur. The parental peanut plant to which the gene or genes from the nonrecurrent parent are transferred is known as the recurrent parent as it is used for several rounds in the backcrossing protocol (Poehlman & Sleper (1994); Fehr, Principles of Cultivar Development, pp. 261-286 (1987)). In a typical backcross protocol, the original variety of interest (recurrent parent) is crossed to a second variety (nonrecurrent parent) that carries the single gene of interest to be transferred. The resulting progeny from this cross are then crossed again to the recurrent parent and the process is repeated until a peanut plant is obtained wherein essentially all of the desired morphological and physiological characteristics of the recurrent parent are recovered in the converted plant, in addition to the single transferred gene from the nonrecurrent parent.

The selection of a suitable recurrent parent is an important step for a successful backcrossing procedure. The goal of a backcross protocol is to alter or substitute a single trait or characteristic in the original variety. To accomplish this, a single gene of the recurrent variety is modified or substituted with the desired gene from the nonrecurrent parent, while retaining essentially all of the rest of the desired genetic, and therefore the desired physiological and morphological constitution of the original variety. The choice of the particular nonrecurrent parent will depend on the purpose of the backcross; one of the major purposes is to add some agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Many single gene traits have been identified that are not regularly selected for in the development of a new variety but that can be improved by backcrossing techniques. Single gene traits may or may not be transgenic. Examples of these traits include, but are not limited to, male sterility, waxy starch, herbicide resistance, resistance for bacterial, fungal, or viral disease, insect resistance, male fertility, enhanced nutritional quality, industrial usage, yield stability, and yield enhancement. These genes are generally inherited through the nucleus. Several of these single gene traits are described in U.S. Pat. Nos. 5,959,185, 5,973,234, and 5,977,445, the disclosures of which are specifically hereby incorporated by reference.

Introduction of a New Trait or Locus into Peanut Cultivar UFT113

Peanut cultivar UFT113 represents a new base genetic variety into which a new locus or trait may be introgressed. Direct transformation and backcrossing represent two important methods that can be used to accomplish such an introgression. The term backcross conversion and single locus conversion are used interchangeably to designate the product of a backcrossing program.

Backcross Conversions of Peanut Cultivar UFT113

A backcross conversion of peanut cultivar UFT113 occurs when DNA sequences are introduced through backcrossing (Hallauer, et al., "Corn Breeding," *Corn and Corn Improvements*, No. 18, pp. 463-481 (1988)), with peanut cultivar UFT113 utilized as the recurrent parent. Both naturally occurring and transgenic DNA sequences may be introduced through backcrossing techniques. A backcross conversion may produce a plant with a trait or locus conversion in at least two or more backcrosses, including at least 2 crosses, at least 3 crosses, at least 4 crosses, at least 5 crosses, and the like. Molecular marker assisted breeding or selection may be utilized to reduce the number of backcrosses necessary to achieve the backcross conversion. For example, see, Openshaw, S. J., et al., Marker-assisted Selection in Backcross Breeding, *Proceedings Symposium of the Analysis of Molecular Data*, Crop Science Society of America, Corvallis, Oreg. (August 1994), where it is demonstrated that a backcross conversion can be made in as few as two backcrosses.

The complexity of the backcross conversion method depends on the type of trait being transferred (single genes or closely linked genes as compared to unlinked genes), the level of expression of the trait, the type of inheritance (cytoplasmic or nuclear), and the types of parents included in the cross. It is understood by those of ordinary skill in the art that for single gene traits that are relatively easy to classify, the backcross method is effective and relatively easy to manage. (See, Hallauer, et al., *Corn and Corn Improvement*, Sprague and Dudley, Third Ed. (1998)). Desired traits that may be transferred through backcross conversion include, but are not limited to, sterility (nuclear and cytoplasmic), fertility restoration, nutritional enhancements, drought tolerance, nitrogen utilization, altered fatty acid profile, low phytate, industrial enhancements, disease resistance (bacterial, fungal, or viral), insect resistance, and herbicide resistance. In addition, an introgression site itself, such as an FRT site, Lox site, or other site specific integration site, may be inserted by backcrossing and utilized for direct insertion of one or more genes of interest into a specific plant variety. In some embodiments of the invention, the number of loci that may be backcrossed into peanut cultivar UFT113 is at least 1, 2, 3, 4, or 5, and/or no more than 6, 5, 4, 3, or 2. A single locus may contain several transgenes, such as a transgene for disease resistance that, in the same expression vector, also contains a transgene for herbicide resistance. The gene for herbicide resistance may be used as a selectable marker and/or as a phenotypic trait. A single locus conversion of site specific integration system allows for the integration of multiple genes at the converted loci.

The backcross conversion may result from either the transfer of a dominant allele or a recessive allele. Selection of progeny containing the trait of interest is accomplished by direct selection for a trait associated with a dominant allele. Transgenes transferred via backcrossing typically function as a dominant single gene trait and are relatively easy to classify. Selection of progeny for a trait that is transferred via a recessive allele requires growing and selfing the first backcross generation to determine which plants carry the recessive alleles. Recessive traits may require additional progeny testing in successive backcross generations to determine the presence of the locus of interest. The last backcross generation is usually selfed to give pure breeding progeny for the gene(s) being transferred, although a backcross conversion with a stably introgressed trait may also be maintained by further backcrossing to the recurrent parent with selection for the converted trait.

Along with selection for the trait of interest, progeny are selected for the phenotype of the recurrent parent. The backcross is a form of inbreeding, and the features of the recurrent parent are automatically recovered after successive backcrosses. Poehlman, *Breeding Field Crops*, p. 204 (1987). Poehlman suggests from one to four or more backcrosses, but as noted above, the number of backcrosses necessary can be reduced with the use of molecular markers. Other factors, such as a genetically similar donor parent, may also reduce the number of backcrosses necessary. As noted by Poehlman, backcrossing is easiest for simply inherited, dominant, and easily recognized traits.

One process for adding or modifying a trait or locus in peanut cultivar UFT113 comprises crossing peanut cultivar UFT113 plants grown from peanut cultivar UFT113 seed with plants of another peanut variety that comprise the desired trait or locus, selecting $F_1$ progeny plants that comprise the desired trait or locus to produce selected $F_1$ progeny plants, crossing the selected progeny plants with the peanut cultivar UFT113 plants to produce backcross progeny plants, selecting for backcross progeny plants that have the desired trait or locus and the morphological characteristics of peanut cultivar UFT113 to produce selected backcross progeny plants, and backcrossing to peanut cultivar UFT113 three or more times in succession to produce selected fourth or higher backcross progeny plants that comprise said trait or locus. The modified peanut cultivar UFT113 may be further characterized as having the physiological and morphological characteristics of peanut variety UFT113 listed in Table 1 as determined at the 5% significance level when grown in the same environmental conditions and/or may be characterized by percent similarity or identity to peanut cultivar UFT113 as determined by SSR markers. The above method may be utilized with fewer backcrosses in appropriate situations, such as when the donor parent is highly related or markers are used in the selection step. Desired traits that may be used include those nucleic acids known in the art, some of which are listed herein, that will affect traits through nucleic acid expression or inhibition. Desired loci include the introgression of FRT, Lox, and other sites for site specific integration, which may also affect a desired trait if a functional nucleic acid is inserted at the integration site.

In addition, the above process and other similar processes described herein may be used to produce first generation progeny peanut seed by adding a step at the end of the process that comprises crossing peanut cultivar UFT113 with the introgressed trait or locus with a different peanut plant and harvesting the resultant first generation progeny peanut seed.

Tissue Culture

Further reproduction of the variety can occur by tissue culture and regeneration. Tissue culture of various tissues of peanuts and regeneration of plants there from is well known and widely published. For example, reference may be had to Komatsuda, T., et al., *Crop Sci.,* 31:333-337 (1991); Stephens, P. A., et al., *Theor. Appl. Genet.,* 82:633-635 (1991); Komatsuda, T., et al., *Plant Cell, Tissue and Organ Culture,* 28:103-113 (1992); Dhir, S., et al., *Plant Cell Reports,* 11:285-289 (1992); Pandey, P., et al., *Japan J. Breed.,* 42:1-5 (1992); and Shetty, K., et al., *Plant Science,* 81:245-251 (1992); as well as U.S. Pat. No. 5,024,944, issued Jun. 18, 1991 to Collins, et al. and U.S. Pat. No. 5,008,200, issued Apr. 16, 1991 to Ranch, et al. Thus, another aspect of this invention is to provide cells which upon growth and differentiation produce peanut plants having the physiological and morphological characteristics of peanut cultivar UFT113.

As used herein, the term "tissue culture" indicates a composition comprising isolated cells of the same or a different type or a collection of such cells organized into parts of a plant. Exemplary types of tissue cultures are protoplasts, calli, plant clumps, and plant cells that can generate tissue culture that are intact in plants or parts of plants, such as embryos, pollen, flowers, seeds, pods, petioles, leaves, stems, roots, root tips, anthers, pistils, and the like. Means for preparing and maintaining plant tissue culture are well known in the art. By way of example, a tissue culture comprising organs has been used to produce regenerated plants. U.S. Pat. Nos. 5,959,185, 5,973,234, and 5,977,445 describe certain techniques, the disclosures of which are incorporated herein by reference.

Using Peanut Cultivar UFT113 to Develop Other Peanut Varieties

Peanut varieties such as peanut cultivar UFT113 are typically developed for use in seed and grain production. However, peanut varieties such as peanut cultivar UFT113 also provide a source of breeding material that may be used to develop new peanut varieties. Plant breeding techniques known in the art and used in a peanut plant breeding program include, but are not limited to, recurrent selection, mass selection, bulk selection, mass selection, backcrossing, pedigree breeding, open pollination breeding, restriction fragment length polymorphism enhanced selection, genetic marker enhanced selection, making double haploids, and transformation. Often combinations of these techniques are used. The development of peanut varieties in a plant breeding program requires, in general, the development and evaluation of homozygous varieties. There are many analytical methods available to evaluate a new variety. The oldest and most traditional method of analysis is the observation of phenotypic traits, but genotypic analysis may also be used.

Choice of breeding or selection methods depends on the mode of plant reproduction, the heritability of the trait(s) being improved, and the type of cultivar used commercially (e.g., $F_1$ hybrid cultivar, pureline cultivar, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection.

The complexity of inheritance influences the choice of breeding method. Backcross breeding is used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Each breeding program should include a periodic, objective evaluation of the efficiency of the breeding procedure. Evaluation criteria vary depending on the goal and objectives, but should include gain from selection per year based on comparisons to an appropriate standard, the overall value of the advanced breeding lines, and the number of successful cultivars produced per unit of input (e.g., per year, per dollar expended, etc.).

Promising advanced breeding lines are thoroughly tested and compared to appropriate standards in environments representative of the commercial target area(s) for at least three years. The best lines are candidates for new commercial cultivars; those still deficient in a few traits are used as parents to produce new generations for further selection.

These processes, which lead to the final step of marketing and distribution, usually take from ten to twenty years from the time the first cross or selection is made. Therefore, development of new cultivars is a time-consuming process that requires precise forward planning, efficient use of resources, and a minimum of changes in direction.

A most difficult task is the identification of individuals that are genetically superior, because for most traits the true genotypic value is masked by other confounding plant traits or environmental factors. One method of identifying a superior plant is to observe its performance relative to other experimental plants and to a widely grown standard cultivar. If a single observation is inconclusive, replicated observations provide a better estimate of its genetic worth.

The goal of peanut plant breeding is to develop new, unique and superior peanut cultivars. The breeder initially selects and crosses two or more parental lines, followed by repeated selfing and selection, producing many new genetic combinations. The breeder can theoretically generate billions of different genetic combinations via crossing, selfing and mutations. The breeder has no direct control at the cellular level. Therefore, two breeders will never develop the same line, or even very similar lines, having the same peanut traits.

Each year, the plant breeder selects the germplasm to advance to the next generation. This germplasm is grown under unique and different geographical, climatic and soil conditions and further selections are then made, during and at the end of the growing season. The cultivars that are developed are unpredictable. This unpredictability is because the breeder's selection occurs in unique environments, with no control at the DNA level (using conventional breeding procedures), and with millions of different possible genetic combinations being generated. A breeder of ordinary skill in the art cannot predict the final resulting lines he/she develops, except possibly in a very gross and general fashion. The same breeder cannot produce the same line twice by using the exact same original parents and the same selection techniques. This unpredictability results in the expenditure of large research monies to develop superior peanut cultivars.

The development of commercial peanut cultivars often starts with crosses between different commercial varieties and/or germplasm at different stages in development. Pedigree breeding and recurrent selection breeding methods are used to develop cultivars from breeding populations. Breeding programs combine desirable traits from two or more varieties or various broad-based sources into breeding pools from which cultivars are developed by selfing and selection of desired phenotypes. The new cultivars are crossed with other varieties and the hybrids from these crosses are evaluated to determine which have commercial potential.

Pedigree breeding is used commonly for the improvement of self-pollinating crops or inbred lines of cross-pollinating crops. Two parents which possess favorable, complementary traits are crossed to produce an $F_1$. An $F_2$ population is produced by selfing one or several $F_1$'s or by intercrossing two $F_1$'s (sib mating). Selection of the best individuals usually begins in the $F_2$ population; then, beginning in the $F_3$, the best individuals in the best families are selected. Replicated testing of families, or hybrid combinations involving individuals of these families, often follows in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new cultivars.

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

Backcross breeding has been used to transfer genes for a simply inherited, highly heritable trait into a desirable homozygous cultivar or line that is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting plant is expected to have the attributes of the recurrent parent (e.g., cultivar) and the desirable trait transferred from the donor parent.

In the strictest sense, the single-seed descent procedure refers to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines each generation due to failure of some seeds to germinate or some plants to produce at least one seed. As a result, not all of the $F_2$ plants originally sampled in the population will be represented by a progeny when generation advance is completed.

In addition to phenotypic observations, the genotype of a plant can also be examined. There are many laboratory-based techniques available for the analysis, comparison and characterization of a plants genotype. Among these are Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length polymorphisms (AFLPs), Simple Sequence Repeats (SSRs—which are also referred to as Microsatellites), and Single Nucleotide Polymorphisms (SNPs).

Isozyme Electrophoresis and RFLPs have been widely used to determine genetic composition. Shoemaker and Olsen, (*Molecular Linkage Map of Soybean* (*Glycine max*) p. 6.131-6.138 in S. J. O'Brien (ed) Genetic Maps: Locus Maps of Complex Genomes, Cold Spring Harbor Laboratory Press, Cold Spring Harbor, N.Y., (1993)) developed a molecular genetic linkage map that consisted of 25 linkage groups with about 365 RFLP, 11 RAPD, three classical markers and four isozyme loci. See also, Shoemaker, R. C., *RFLP Map of Soybean*, p 299-309, in Phillips, R. L. and Vasil, I. K., eds. *DNA-Based Markers in Plants*, Kluwer Academic Press, Dordrecht, the Netherlands (1994).

SSR technology is currently the most efficient and practical marker technology; more marker loci can be routinely used and more alleles per marker locus can be found using SSRs in comparison to RFLPs. For example, Diwan and Cregan described a highly polymorphic microsatellite locus in soybean with as many as 26 alleles. (Diwan, N. and Cregan, P. B., *Theor. Appl. Genet.* 95:22-225, 1997.) SNPs may also be used to identify the unique genetic composition of the invention and progeny varieties retaining that unique genetic composition. Various molecular marker techniques may be used in combination to enhance overall resolution.

Molecular markers, which include markers identified through the use of techniques such as Isozyme Electrophoresis, RFLPs, RAPDs, AP-PCR, DAF, SCARs, AFLPs, SSRs, and SNPs, may be used in plant breeding. One use of molecular markers is Quantitative Trait Loci (QTL) mapping. QTL mapping is the use of markers which are known to be closely linked to alleles that have measurable effects on a quantitative trait. Selection in the breeding process is based upon the accumulation of markers linked to the positive effecting alleles and/or the elimination of the markers linked to the negative effecting alleles from the plant's genome.

Molecular markers can also be used during the breeding process for the selection of qualitative traits. For example, markers closely linked to alleles or markers containing sequences within the actual alleles of interest can be used to select plants that contain the alleles of interest during a backcrossing breeding program. The markers can also be used to select toward the genome of the recurrent parent and against the markers of the donor parent. This procedure attempts to minimize the genomic contribution from the donor parent that remains in the selected plants, and can reduce the number of back-crosses necessary to generate coisogenic plants. This procedure is often called genetic marker enhanced selection or marker-assisted selection. Molecular markers may also be used to identify and exclude certain sources of germplasm as parental varieties or ancestors of a plant by providing a means of tracking genetic profiles through crosses.

Mutation breeding is another method of introducing new traits into peanut varieties. Mutations that occur spontaneously or are artificially induced can be useful sources of variability for a plant breeder. The goal of artificial mutagenesis is to increase the rate of mutation for a desired characteristic. The use of mutagenic agents to create genetic diversity in peanuts as well as useful peanut mutants has been described by Norden, A. J., et al., Breeding of the cultivated peanut in *Peanut Science and Technology*, the entirety of which is incorporated herein by reference. Peanut mutants may be induced by γ-irradiation according to the method of Sharma, et al. *Qual. Plant Foods Hum. Nutr.* 35:3-8 (1985), the entirety of which is incorporated herein by reference. Methods for inducing mutation in peanut seeds chemically are also available in Ashri, A. Mutation Research, 9:473-480 (1970).

The production of double haploids can also be used for the development of homozygous varieties in a breeding program. Double haploids are produced by doubling a set of chromosomes from a heterozygous plant to produce a completely homozygous individual. For example, see Wan et al., *Theor. Appl. Genet.*, 77:889-892, 1989.

Descriptions of other breeding methods that are commonly used for different traits and crops can be found in several reference books (e.g., *Principles of Plant Breeding* John Wiley and Son, pp. 115-161, 1960; Allard, 1960; Simmonds, 1979; Sneep et al., 1979; Fehr, 1987; Carrots and Related Vegetable *Umbelliferae*, Rubatzky, V. E., et al., 1999).

Proper testing should detect any major faults and establish the level of superiority or improvement over current cultivars. In addition to showing superior performance, there must be a demand for a new cultivar that is compatible with industry standards or which creates a new market. The introduction of a new cultivar will incur additional costs to the seed producer, the grower, processor and consumer for special advertising and marketing, altered seed and commercial production practices, and new product utilization. The testing preceding release of a new cultivar should take into consideration research and development costs as well as technical superiority of the final cultivar. For seed-propagated cultivars, it must be feasible to produce seed easily and economically.

Additional Breeding Methods

The following describes breeding methods that may be used with peanut cultivar UFT113 in the development of further peanut plants. One such embodiment is a method for developing a cultivar UFT113 progeny peanut plant in a peanut plant breeding program comprising: obtaining the peanut plant, or a part thereof, of cultivar UFT113, utilizing said plant, or plant part, as a source of breeding material, and selecting a peanut cultivar UFT113 progeny plant with molecular markers in common with cultivar UFT113 and/or with morphological and/or physiological characteristics selected from the characteristics described in the Tables. Breeding steps that may be used in the peanut plant breeding program include pedigree breeding, backcrossing, mutation breeding, and recurrent selection. In conjunction with these steps, techniques such as RFLP-enhanced selection, genetic marker enhanced selection (for example, SSR markers), and the making of double haploids may be utilized.

Another method involves producing a population of peanut cultivar UFT113 progeny peanut plants, comprising crossing cultivar UFT113 with another peanut plant, thereby producing a population of peanut plants which, on average, derive 50% of their alleles from peanut cultivar UFT113. A plant of this population may be selected and repeatedly selfed or sibbed with a peanut cultivar resulting from these successive filial generations. One embodiment of this invention is the peanut cultivar produced by this method and that has obtained at least 50% of its alleles from peanut cultivar UFT113.

One of ordinary skill in the art of plant breeding would know how to evaluate the traits of two plant varieties to determine if there is no significant difference between the two traits expressed by those varieties. For example, see, Fehr and Walt, *Principles of Cultivar Development*, pp. 261-286 (1987). Thus the invention includes peanut cultivar UFT113 progeny peanut plants comprising a combination of at least two cultivar UFT113 traits selected from the group consisting of those listed in Table 1 or the cultivar UFT113 combination of traits listed in the Summary of the Invention, so that said progeny peanut plant is not significantly different for said traits than peanut cultivar UFT113 as determined at the 5% significance level when grown in the same environmental conditions. Using techniques described herein, molecular markers may be used to identify said progeny plant as a peanut cultivar UFT113 progeny plant. Mean trait values may be used to determine whether trait differences are significant, and preferably the traits are measured on plants grown under the same environmental conditions. Once such a variety is developed, its value is substantial since it is important to advance the germplasm base as a whole in order to maintain or improve traits such as yield, disease resistance, pest resistance, and plant performance in extreme environmental conditions.

Progeny of peanut cultivar UFT113 may also be characterized through their filial relationship with peanut cultivar UFT113, as for example, being within a certain number of breeding crosses of peanut cultivar UFT113. A breeding cross is a cross made to introduce new genetics into the progeny, and is distinguished from a cross, such as a self or a sib cross, made to select among existing genetic alleles. The lower the number of breeding crosses in the pedigree, the closer the relationship between peanut cultivar UFT113 and its progeny. For example, progeny produced by the methods described herein may be within 1, 2, 3, 4, or 5 breeding crosses of peanut cultivar UFT113.

As used herein, the term "plant" includes plant cells, plant protoplasts, plant cell tissue cultures from which peanut plants can be regenerated, plant calli, plant clumps, and plant cells that are intact in plants or parts of plants, such as embryos, pollen, ovules, flowers, pods, leaves, roots, root tips, anthers, cotyledons, hypocotyls, meristematic cells, stems, pistils, petiole, and the like.

Pedigree Breeding

Pedigree breeding starts with the crossing of two genotypes, such as peanut cultivar UFT113 and another peanut variety having one or more desirable characteristics that is lacking or which complements peanut cultivar UFT113. If the two original parents do not provide all the desired characteristics, other sources can be included in the breeding population. In the pedigree method, superior plants are selfed and selected in successive filial generations. In the succeeding filial generations, the heterozygous condition gives way to homogeneous varieties as a result of self-pollination and selection. Typically in the pedigree method of breeding, five or more successive filial generations of selfing and selection is practiced: $F_1$ to $F_2$; $F_2$ to $F_3$; $F_3$ to $F_4$; $F_4$ to $F_5$; etc. After a sufficient amount of inbreeding, successive filial generations will serve to increase seed of the developed variety. Preferably, the developed variety comprises homozygous alleles at about 95% or more of its loci.

In addition to being used to create a backcross conversion, backcrossing can also be used in combination with pedigree breeding. As discussed previously, backcrossing can be used to transfer one or more specifically desirable traits from one variety, the donor parent, to a developed variety called the recurrent parent, which has overall good agronomic characteristics yet lacks that desirable trait or traits. However, the same procedure can be used to move the progeny toward the genotype of the recurrent parent, but at the same time retain many components of the nonrecurrent parent by stopping the backcrossing at an early stage and proceeding with selfing and selection. For example, a peanut variety may be crossed with another variety to produce a first generation progeny plant. The first generation progeny plant may then be backcrossed to one of its parent varieties to create a $BC_1$ or $BC_2$. Progeny are selfed and selected so that the newly developed variety has many of the attributes of the recurrent parent and yet several of the desired attributes of the nonrecurrent parent. This approach leverages the value and strengths of the recurrent parent for use in new peanut varieties.

Therefore, an embodiment of this invention is a method of making a backcross conversion of peanut cultivar UFT113, comprising the steps of crossing a plant of peanut cultivar UFT113 with a donor plant comprising a desired trait, selecting an $F_1$ progeny plant comprising the desired trait, and backcrossing the selected $F_1$ progeny plant to a plant of peanut cultivar UFT113. This method may further comprise the step of obtaining a molecular marker profile of peanut cultivar UFT113 and using the molecular marker profile to select for a progeny plant with the desired trait and the molecular marker profile of peanut cultivar UFT113. In one embodiment, the desired trait is a mutant gene or transgene present in the donor parent.

Recurrent Selection and Mass Selection

Recurrent selection is a method used in a plant breeding program to improve a population of plants. Peanut cultivar UFT113 is suitable for use in a recurrent selection program. The method entails individual plants cross pollinating with each other to form progeny. The progeny are grown and the superior progeny selected by any number of selection methods, which include individual plant, half-sib progeny, full-sib progeny, and selfed progeny. The selected progeny are cross pollinated with each other to form progeny for another population. This population is planted and again superior plants are selected to cross pollinate with each other. Recurrent selection is a cyclical process and therefore can be repeated as many times as desired. The objective of recurrent selection is to improve the traits of a population. The improved population can then be used as a source of breeding material to obtain new varieties for commercial or breeding use, including the production of a synthetic cultivar. A synthetic cultivar is the resultant progeny formed by the intercrossing of several selected varieties.

Mass selection is a useful technique when used in conjunction with molecular marker enhanced selection. In mass selection, seeds from individuals are selected based on phenotype or genotype. These selected seeds are then bulked and used to grow the next generation. Bulk selection requires growing a population of plants in a bulk plot, allowing the plants to self-pollinate, harvesting the seed in bulk, and then using a sample of the seed harvested in bulk to plant the next generation. Also, instead of self pollination, directed pollination could be used as part of the breeding program.

Mutation Breeding

Mutation breeding is another method of introducing new traits into peanut cultivar UFT113. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation; such as X-rays, Gamma rays (e.g., cobalt 60 or cesium 137), neutrons, (product of nuclear fission by uranium 235 in an atomic reactor), Beta radiation (emitted from radioisotopes such as phosphorus 32 or carbon 14), or ultraviolet radiation (preferably from 2500 to 2900 nm), or chemical mutagens (such as base analogues (5-bromo-uracil)), related compounds (8-ethoxy caffeine), alkylating agents (sulfur mustards, nitrogen mustards, epoxides, ethylenamines, sulfates, sulfonates, sulfones, lactones), azide, hydroxylamine, nitrous acid, or acridines. Once a desired trait is observed through mutagenesis the trait may then be incorporated into existing germplasm by traditional breeding techniques. Details of mutation breeding can be found in Fehr, "Principles of Cultivar Development," Macmillan Publishing Company (1993). In addition, mutations created in other peanut plants may be used to produce a backcross conversion of peanut cultivar UFT113 that comprises such mutation.

Breeding with Molecular Markers

Molecular markers, which includes markers identified through the use of techniques such as Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs), and Single Nucleotide Polymorphisms (SNPs), may be used in plant breeding methods utilizing peanut cultivar UFT113.

Isozyme Electrophoresis and RFLPs have been widely used to determine genetic composition. Shoemaker and Olsen, Molecular Linkage Map of Soybean (*Glycine max* L. Merr.), pp. 6.131-6.138 (1993). In S. J. O'Brien (ed.), *Genetic Maps: Locus Maps of Complex Genomes*, Cold Spring Harbor Laboratory Press, Cold Spring Harbor, N.Y., developed a molecular genetic linkage map that consisted of 25 linkage groups with about 365 RFLP, 11 RAPD (random amplified polymorphic DNA), 3 classical markers, and 4 isozyme loci. See also, Shoemaker, R. C., 1994 RFLP Map of Soybean, pp. 299-309; In R. L. Phillips and I. K. Vasil (ed.), *DNA-based markers in plants*, Kluwer Academic Press Dordrecht, the Netherlands.

SSR technology is currently the most efficient and practical marker technology. More marker loci can be routinely used, and more alleles per marker locus can be found, using SSRs in comparison to RFLPs. For example, Diwan and Cregan described a highly polymorphic microsatellite loci in soybean with as many as 26 alleles. (Diwan, N., and Cregan. P. B., Automated sizing of fluorescent-labeled simple sequence repeat (SSR) markers to assay genetic variation in Soybean, *Theor. Appl. Genet.*, 95:220-225 (1997). Single Nucleotide Polymorphisms may also be used to identify the unique genetic composition of the invention and progeny varieties retaining that unique genetic composition. Various molecular marker techniques may be used in combination to enhance overall resolution.

One use of molecular markers is Quantitative Trait Loci (QTL) mapping. QTL mapping is the use of markers, which are known to be closely linked to alleles that have measurable effects on a quantitative trait. Selection in the breeding process is based upon the accumulation of markers linked to the positive effecting alleles and/or the elimination of the markers linked to the negative effecting alleles from the plant's genome. Molecular markers can also be used during the breeding process for the selection of qualitative traits. For example, markers closely linked to alleles or markers containing sequences within the actual alleles of interest can be used to select plants that contain the alleles of interest during a backcrossing breeding program. The markers can also be used to select for the genome of the recurrent parent and against the genome of the donor parent. Using this procedure can minimize the amount of genome from the donor parent that remains in the selected plants. It can also be used to reduce the number of crosses back to the recurrent parent needed in a backcrossing program. The use of molecular markers in the selection process is often called genetic marker enhanced selection. Molecular markers may also be used to identify and exclude certain sources of germplasm as parental varieties or ancestors of a plant by providing a means of tracking genetic profiles through crosses.

Production of Double Haploids

The production of double haploids can also be used for the development of plants with a homozygous phenotype in the breeding program. For example, a peanut plant for which peanut cultivar UFT113 is a parent can be used to produce double haploid plants. Double haploids are produced by the doubling of a set of chromosomes (1 N) from a heterozygous plant to produce a completely homozygous individual. For example, see, Wan, et al., "Efficient Production of Doubled Haploid Plants Through Colchicine Treatment of Anther-Derived Maize Callus," *Theoretical and Applied Genetics*, 77:889-892 (1989) and U.S. Pat. No. 7,135,615. This can be advantageous because the process omits the generations of selfing needed to obtain a homozygous plant from a heterozygous source.

Haploid induction systems have been developed for various plants to produce haploid tissues, plants and seeds. The haploid induction system can produce haploid plants from any genotype by crossing a selected line (as female) with an inducer line. Such inducer lines for maize include Stock 6 (Coe, *Am. Nat.*, 93:381-382 (1959); Sharkar and Coe, *Genetics*, 54:453-464 (1966); KEMS (Deimling, Roeber, and Geiger, *Vortr. Pflanzenzuchtg*, 38:203-224 (1997); or KMS and ZMS (Chalyk, Bylich & Chebotar, *MNL*, 68:47 (1994); Chalyk & Chebotar, *Plant Breeding*, 119:363-364 (2000)); and indeterminate gametophyte (ig) mutation (Kermicle, *Science*, 166:1422-1424 (1969). The disclosures of which are incorporated herein by reference.

Methods for obtaining haploid plants are also disclosed in Kobayashi, M., et al., Journ. of Heredity, 71(1):9-14 (1980); Pollacsek, M., Agronomie (Paris) 12(3):247-251 (1992); Cho-Un-Haing, et al., *Journ. of Plant Biol.*, 39(3):185-188 (1996); Verdoodt, L., et al., 96(2):294-300 (February 1998); Genetic Manipulation in Plant Breeding, Proceedings International Symposium Organized by EUCARPIA, Berlin, Germany (Sep. 8-13, 1985); Chalyk, et al., *Maize Genet Coop.*, Newsletter 68:47 (1994).

Thus, an embodiment of this invention is a process for making a substantially homozygous peanut cultivar UFT113 progeny plant by producing or obtaining a seed from the cross of peanut cultivar UFT113 and another peanut plant and applying double haploid methods to the $F_1$ seed or $F_1$ plant or to any successive filial generation. Based on studies in maize and currently being conducted in soybean, such methods would decrease the number of generations required to produce a variety with similar genetics or characteristics to peanut cultivar UFT113. See, Bernardo, R. and Kahler, A. L., *Theor. Appl. Genet.*, 102:986-992 (2001).

In particular, a process of making seed retaining the molecular marker profile of peanut cultivar UFT113 is contemplated, such process comprising obtaining or producing $F_1$ seed for which peanut cultivar UFT113 is a parent, inducing doubled haploids to create progeny without the occurrence of meiotic segregation, obtaining the molecular marker profile of peanut cultivar UFT113, and selecting progeny that retain the molecular marker profile of peanut cultivar UFT113.

Descriptions of other breeding methods that are commonly used for different traits and crops can be found in one of several reference books (e.g., Allard (1960); Simmonds (1979); Sneep, et al. (1979); Fehr (1987)).

INDUSTRIAL USES

The TSWV resistance trait can be introgressed into other varieties in the runner-type market class (*A. hypogaea* subsp. *hypogaea* var. *hypogaea* botanical type Virginia) as well as the Virginia (*A. hypogaea* subsp. *hypogaea* var. *hypogaea* botanical type Virginia), Peruvian (*A. hypogaea* subsp. *hypogaea* var. *hypogaea* botanical type Peruvian runner), Valencia (*A. hypogaea* subsp. *fastigata* var. *fastigata* botanical type Valencia), and Spanish (*A. hypogaea* subsp. *fastigata* var. *vulgaris* botanical type Spanish) market classes. Peanuts in the runner-type market class are the most commonly used varieties and are found in diverse products such as peanut butter, salted nuts and confectionery products. On the other hand, peanut varieties in the Virginia market class are largely used as salted nuts and in-shell market. The Valencia is largely used in peanut butter while the Spanish type is used in certain niche markets where small round peanuts are needed such as confectionery products and red skin peanuts. Finally, the Peruvian runner market class is grown in certain regions of Mexico.

Peanut is recognized as one of the major oilseed crops and as a rich source of protein. In the United States peanuts are primarily utilized as whole seeds for human foods such as peanut butter, roasted seeds, and confections. In recent years the United States has been the leading exporter of peanuts for human consumption; peanuts rank ninth in area among the row crops and second in dollar value per acre. Peanuts are rich in nutrients, providing over 30 essential nutrients and phytonutrients, and are a good source of niacin, folate, fiber, magnesium, vitamin E, manganese and phosphorus. They are also naturally free of trans-fats and sodium, and contain about 25% protein. Because of these qualities, organizations like the World Heath Organization, UNICEF, Project Peanut Butter and Doctors Without Borders have used peanut products to help save malnourished children in developing countries. Thus, improvement of the factors that indicate and/or affect both the food quality of peanuts and the peanut harvest is of considerable importance to the worldwide peanut processing and manufacturing community.

TABLES

In the Tables that follow, the Disease Risk Index for TSWV for peanut cultivar UFT113 compared with other commercially available lines is shown.

Peanut Disease Risk Index

The Spotted Wilt Index and the Peanut Fungal Disease Risk Index were successfully combined in 2005 to produce the Peanut Disease Risk Index for peanut producers in the southeastern United States. The Peanut Disease Risk Index, developed by researchers and Extension specialists at the University of Georgia, the University of Florida, and Auburn University, is now officially known as "PEANUT Rx". Tomato spotted wilt virus (TSWV) can cause a disease that severely weakens or kills the host plant and is capable of infecting an unusually large number of plant species including several that are important crops in the southeastern United States, such as the peanut. Weather patterns in Georgia and neighboring areas during the growing season create the near-perfect environmental conditions for outbreaks of fungal diseases, such as early and late leaf spot, rust, *Rhizoctonia limb* rot, southern stem rot (referred to locally as "white mold"), Cylindrocladium black rot and a host of other diseases that are common, but of sporadic importance. If peanut growers do not take appropriate measures to manage fungal diseases, crop loss in a field may exceed 50%.

Many factors combine to influence the risk of losses to spotted wilt and fungal disease in a peanut crop. These factors include: peanut variety, planting date, plant population, insecticide use, row pattern, tillage, crop rotation, field history and irrigation. Some factors are more important than others, but no single factor can be used as a reliable TSWV control measure. However, research data and on-farm observations indicate that when combinations of several factors are considered, an individual field's risk of losses due to TSWV can be estimated. There is no way to predict with total accuracy how much TSWV will occur in a given situation or how the disease will affect yield, but by identifying high risk situations, growers can avoid those production practices that are conducive to major yield losses. The index combines what is known about individual risk factors into a comprehensive, but simple, estimate of TSWV risk for a given field. It assigns a relative importance to each factor so that an overall level of risk can be estimated.

The Peanut Rx is based upon better understanding of factors that affect disease incidence and severity. It is designed to help growers approximate the magnitude of the risk that they face from foliar and soilborne diseases in the coming season. More importantly, it should serve as an educational tool that allows the grower to predict the benefits of different management practices he makes in hopes of producing a better crop. The risks associated with leaf spot, white mold and *Rhizoctonia limb* rot diseases are to be determined independently in the index system to be presented here. The magnitude of points associated with each variable is not linked between soilborne and foliar disease categories. However, the points allotted to each variable in the PEANUT Rx are weighted within a disease category according to the importance of the variable (such as variety or field history) to another variable (such as planting date). For example, within the category for leaf spot diseases, a maximum of 30 points is allotted to the variable "variety" while 0 points is allotted to the variable "row pattern". For each of the following factors that can influence the incidence of tomato spotted wilt or fungal diseases, the grower or consultant should identify which option best describes the situation for an individual peanut field. Add the index numbers associated with each choice to obtain an overall risk index value. Compare that number to the risk scale provided and identify the projected level of risk.

Table 2 show the results of TSWV testing (presence) in peanut cultivar UFT113 compared with commercial cultivars Georgia Green and Florida-07. Data was collected in 2010 from two locations in Florida: Marianna and Quincy. 100 root crown samples were tested for presence (positive) or absence (negative) of the virus that causes TSWV of peanut. ImmunoStrip data was taken from AgDia ImmunoStrip test kits. Column one shows the test location, column two shows the cultivar line, column three shows the TSWV rating on a 1-10 scale where 1=less than 10% disease and 10=greater than 90% disease, column four shows the TSWV hit count where each whole number corresponds to 1 linear foot (12 inches) of row diseased (the plot length was 30 feet, therefore the maximum hit count is 30), column five shows pod yield in pounds per acre, and columns six and seven show the percentage of plants which tested negative or positive for TSWV based on ImmunoStrip testing of the root crown. Values in the Peanut Rx are assigned relative to known genotypes like Georgia Green based on data such as presented in Table 2 and Tables 3-7 below. Peanut cultivar UFT113 is unique in regard to TSWV infection. Previous reports of TSWV infection showed that at least 60% of the plants of even the most resistant cultivars (Like DP-1 (Gorbet and Tillman, 2008)) were infected with TSWV as measured in the root crown (Murakami et al., 2006; Rowland et al., 2005).

TABLE 2

Comparison of peanut cultivar UFT113 to Georgia Green and Florida-07 in 2010 in two Florida locations.

| Location | Line | TSWV 1-10 rating | TSWV Hit Count # out of 30 | Pod Yield lbs./A | Immuno-strip Negative % | Immuno-strip Positive % |
|---|---|---|---|---|---|---|
| Marianna | Florida-07 (UF04327) 96x70-HO3-7-1-1-b3-B | 1.3 | 0.4 | 5027 | 70 | 30 |
| Marianna | Georgia Green | 2.0 | 2.9 | 3728 | 54 | 46 |
| Marianna | UFT113 (02x26-1-B2-1-1-3) | 1.1 | 0.1 | 3965 | 98 | 2 |
| LSD | | 0.5 | 1.6 | 406 | 15 | 15 |
| Quincy | Florida-07 (UF04327) 96x70-HO3-7-1-1-b3-B | 1.4 | 1.4 | 4938 | 49 | 51 |
| Quincy | Georgia Green | 1.5 | 1.9 | 4421 | 48 | 52 |
| Quincy | UFT113 (02x26-1-B2-1-1-3) | 1.1 | 0.4 | 3628 | 96 | 4 |
| LSD | | 0.4 | 1.2 | 361 | 21 | 21 |

As shown in Table 2, Peanut Cultivar UFT113 has a lower TSWV rating, lower TSWV hit count, and significantly fewer TSWV infected plants than commercial cultivars based on ImmunoStrip testing.

Tables 3-7 show data from 2007 (Table 3; planted May 23, 2007 and harvested Oct. 5, 2007 after 135 days), 2008 (Table 4; planted May 29, 2008 and harvested Oct. 13, 2008 after 137 days), and 2010 (Table 5; planted May 13, 2010 and harvested Sep. 17, 2010 after 127 days) collected in Marianna Florida, and Tables 6 and 7 show data from 2009 and 2010 (respectively) collected in three locations: Marianna, Citra, and Jay, Florida (averaged in columns one through thirteen). In Table 6, peanuts were planted May 12, 2009 and harvested Sep. 25, 2009 after 136 days in Marianna; planted May 15, 2009 and harvested Sep. 29, 2009 after 137 days in Jay; and planted Apr. 22, 2009 and harvested Sep. 3, 2009 after 134 days in Citra. In Table 7, peanuts were planted May 11, 2010 and harvested Sep. 20, 2010 after 132 days in Marianna; planted May 13, 2010 and harvested Sep. 24, 2010 after 134 days in Jay; planted April 20 and harvested on Sep. 2, 2010 after 132 days in Citra. Column one shows the cultivar, column two shows the pod yield in pounds per acre, column three shows the TSWV rating, column four shows the percentage of total sound mature kernels, column five shows the percentage of sound mature kernels, column six shows the percentage of sound splits, column seven shows the percentage of Virginia pods, column eight shows the weight of 100 seeds in grams, column nine shows the percentage of number 1 kernels, column ten shows the percentage of medium kernels, column eleven shows the percentage of extra large kernels, column twelve shows the percentage of total meats, column thirteen shows the percentage of other kernels, and column fourteen shows the oleic acid percentage content based on the NIR method. Above 70% is considered high oleic by the NIR method described by Tillman et al., 2006.

TABLE 3

Comparison of UFT113 to commercial cultivars in 2007 in Marianna, Florida.
TSWV disease was relatively severe in this test.

| Line | Pod yield lbs/A | TSWV rating 1-10 | Total Sound Mature Kernels % | Sound Mature Kernels % | Sound Splits % | VA Pods % | Weight of 100 seeds g | No. 1 Kernels % | Medium Kernels % | Extra Large Kernels % | Total Meats % | Other Kernels % | Oleic Acid-NIR** % |
|---|---|---|---|---|---|---|---|---|---|---|---|---|---|
| UFT113 | 5479 | 3.0 | 80.1 | 68.7 | 11.4 | 14.5 | 82.8 | 3.4 | 46.5 | 18.9 | 80.1 | 0.0 | 63.1 |
| Florida-07 | 5053 | 4.0 | 77.0 | 70.5 | 6.6 | 57.9 | 81.2 | 2.3 | 32.9 | 35.4 | 77.1 | 0.2 | 80.2 |
| AP-4 | 4937 | 3.5 | 76.1 | 70.2 | 5.9 | 8.6 | 73.9 | 3.7 | 37.8 | 28.8 | 76.4 | 0.4 | 66.6 |

TABLE 4

Comparison of UFT113 to commercial cultivars in 2008 in Marianna, Florida.
TSWV disease was relatively mild in this test.

| Line | Pod yield lbs/A | TSWV rating 1-10 | Total Sound Mature Kernels % | Sound Mature Kernels % | Sound Splits % | VA Pods % | Weight of 100 seeds g | No. 1 Kernels % | Medium Kernels % | Extra Large Kernels % | Total Meats % | Other Kernels % | Oleic Acid-NIR** % |
|---|---|---|---|---|---|---|---|---|---|---|---|---|---|
| UFT113 | 4216 | 1.0 | 80.9 | 74.6 | 6.4 | 14.0 | 76.4 | 5.8 | 36.0 | 32.8 | 81.4 | 0.5 | 63.6 |
| Georgia-06G | 4487 | 1.0 | 81.1 | 74.0 | 7.1 | 16.8 | 66.0 | 3.1 | 30.6 | 40.4 | 81.3 | 0.2 | 57.5 |
| AP-4 | 4289 | 1.5 | 78.4 | 73.5 | 4.9 | 5.7 | 67.4 | 1.7 | 34.4 | 37.5 | 78.8 | 0.4 | 63.2 |
| LSD | 846 | 0.3 | | | | | | | | | | | |

TABLE 5

Comparison of UFT113 to commercial cultivars in 2010 in Marianna, Florida.
Visual symptoms of spotted wilt disease were not detected in this test.

| Line | Pod yield lbs/A | Yield Rank | TSWV rating 1-10 | Total Sound Mature Kernels % | Sound Mature Kernels % | Sound Splits % | VA Pods % | Weight of 100 seeds g | No. 1 Kernels % | Medium Kernels % | Extra Large Kernels % | Total Meats % | Other Kernels % | Oleic Acid-NIR** % |
|---|---|---|---|---|---|---|---|---|---|---|---|---|---|---|
| AP-4 | 4947 | 22 | No visual symptoms | 77.6 | 74.1 | 3.6 | 14.3 | 76.3 | 2.7 | 27.9 | 43.6 | 78.1 | 0.5 | 60.2 |
| Florida-07 | 5792 | 14 | | 75.9 | 74.2 | 1.8 | 64.7 | 68.7 | 2.2 | 25.1 | 46.9 | 76.3 | 0.4 | 74.6 |
| Georgia-06G | 6137 | 9 | | 79.0 | 77.0 | 2.1 | 68.7 | 76.6 | 1.1 | 20.4 | 55.6 | 79.4 | 0.4 | 60.4 |
| Georgia-07W | 5795 | 13 | | 78.1 | 74.2 | 3.9 | 51.8 | 73.9 | 1.3 | 26.5 | 46.4 | 78.9 | 0.9 | 58.2 |
| UFT113 | 5127 | 21 | | 78.7 | 76.6 | 2.2 | 20.1 | 73.1 | 3.3 | 42.9 | 30.5 | 79.3 | 0.6 | 60.5 |
| LSD | 754 | | | 2.9 | 9.4 | 9.3 | 12.1 | 11.1 | 2.5 | 8.4 | 12.0 | 2.6 | 0.9 | |

**NIR ≥ 70% is high oleic

TABLE 6

Comparison of peanut cultivar UFT113 to commercial cultivars in 2009 in Marianna, Jay, and Citra, Florida.
TSWV was relatively mild in this test.

| | Average over all three locations | | | | | | | | | | |
|---|---|---|---|---|---|---|---|---|---|---|---|
| Line | Pod yield lbs/A | Yield Rank | TSWV rating 1-10 | Total Sound Mature Kernels % | Sound Mature Kernels % | Sound Splits % | VA Pods % | Weight of 100 seeds g | No. 1 Kernels % | Medium Kernels % | Extra Large Kernels % |
| UFT113 | 5198 | 16 | 1.0 | 79.8 | 74.8 | 5.0 | 24.5 | 79.5 | 3.7 | 37.0 | 34.1 |
| AP-4 | 5415 | 11 | 1.3 | 77.6 | 71.3 | 6.4 | 7.9 | 68.5 | 4.1 | 33.8 | 33.4 |
| Georgia Greener | 5838 | 4 | 1.0 | 80.0 | 73.9 | 6.1 | 18.1 | 68.0 | 2.6 | 34.6 | 36.8 |
| Georgia-06G | 5556 | 6 | 1.1 | 80.0 | 74.4 | 5.7 | 47.0 | 71.7 | 2.0 | 26.7 | 45.8 |
| Georgia-07W | 6135 | 1 | 1.1 | 80.4 | 73.4 | 7.0 | 40.9 | 68.2 | 1.7 | 33.7 | 38.0 |
| Florida-07 | 5942 | 2 | 1.0 | 76.1 | 69.1 | 7.0 | 62.3 | 77.3 | 1.4 | 21.8 | 45.9 |
| LSD | 441 | 0 | 0.3 | 0.8 | 1.9 | 1.8 | 6.8 | 3.7 | 1.1 | 3.5 | 4.0 |

| | Average over all three locations | | | Marianna | | Citra | | | Jay | |
|---|---|---|---|---|---|---|---|---|---|---|
| | | | Oleic | | | | | | | |
| Line | Total Meats % | Other Kernels % | Acid-NIR** % | Pod yield lbs/A | Yield Rank | Total Sound Mature Kernels % | Pod yield % | Yield Rank | Total Sound Mature Kernels % | Pod yield g | Yield Rank % |
| UFT113 | 80.6 | 0.8 | 63.8 | 5314 | 9 | 80.2 | 5869 | 22 | 79.5 | 4375 | 19 |
| AP-4 | 78.9 | 1.4 | 65.9 | 4947 | 17 | 78.4 | 6398 | 13 | 76.8 | 4863 | 7 |
| Georgia Greener | 80.8 | 0.8 | 60.0 | 5242 | 10 | 80.2 | 6628 | 6 | 79.8 | 5553 | 1 |
| Georgia-06G | 81.1 | 1.1 | 61.0 | 5174 | 12 | 79.4 | 6937 | 4 | 80.6 | 4588 | 15 |
| Georgia-07W | 80.9 | 0.5 | 61.0 | 6047 | 2 | 80.4 | 6912 | 5 | 80.4 | 5513 | 2 |
| Florida-07 | 76.8 | 0.8 | 80.0 | 6066 | 1 | 75.8 | 7054 | 3 | 76.4 | 4728 | 12 |
| LSD | 0.6 | 0.5 | 5.6 | 402 | | 0.9 | 521 | | 1 | 1003 | |

**NIR ≧ 70% is high oleic

TABLE 7

Comparison of peanut cultivar UFT113 to commercial cultivars in 2010 in Marianna, Jay, and Citra, Florida.
TSWV was relatively mild in this test.

| | Average over all three locations | | | | | | | | | | |
|---|---|---|---|---|---|---|---|---|---|---|---|
| Line | Pod yield lbs/A | Yield Rank | TSWV rating 1-10 | Total Sound Mature Kernels % | Sound Mature Kernels % | Sound Splits % | VA Pods % | Weight of 100 seeds g | No. 1 Kernels % | Medium Kernels % | Extra Large Kernels % |
| UFT113 | 5564 | 17 | 1.1 | 79.5 | 75.5 | 4.0 | 14.3 | 74.3 | 4.1 | 36.0 | 35.5 |
| AP-4 | 5825 | 11 | 1.2 | 77.6 | 72.5 | 5.2 | 21.0 | 75.1 | 3.0 | 23.4 | 46.1 |
| Georgia-07W | 6792 | 1 | 1.1 | 79.1 | 73.8 | 5.3 | 45.6 | 76.0 | 2.6 | 22.4 | 48.9 |
| LSD | 179 | | 0.1 | 0.9 | 1.1 | 0.6 | 1.9 | 1.1 | 0.4 | 1.0 | 1.5 |

| | Average over all three locations | | | Marianna | | Citra | | | Jay | |
|---|---|---|---|---|---|---|---|---|---|---|
| | | | Oleic | | | Total | | | Total | |
| Line | Total Meats % | Other Kernels % | Acid-NIR** % | Pod yield lbs/A | Yield Rank | Sound Mature Kernels % | Pod yield % | Yield Rank | Sound Mature Kernels % | Pod yield g | Yield Rank % |
| UFT113 | 81.0 | 1.5 | 61.0 | 5392 | 20 | 79.1 | 5269 | 20 | 80.0 | 6031 | 6 |
| AP-4 | 79.1 | 1.4 | 58.2 | 6331 | 10 | 77.9 | 5534 | 14 | 77.4 | 5611 | 15 |
| Georgia-07W | 80.3 | 1.2 | 57.7 | 7215 | 1 | 78.7 | 6176 | 1 | 79.5 | 6986 | 1 |
| LSD | 0.4 | 0.2 | | 905 | | 4.2 | 821 | | 6.4 | 1006 | |

**NIR ≧ 70% is high oleic

As shown in the above Tables 3-7, peanut cultivar UFT113 consistently has good yield, excellent grade and very low levels of spotted wilt.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

REFERENCES CITED

Gorbet D. W., Tillman B. L. (2008) Registration of 'DP-1' Peanut. Journal of Plant Registrations 2:200-204. DOI: 10.3198/jpr2007.11.0629crc.

Murakami A., Gallo-Meagher M., Gorbet D. W., Meagher R. L. (2006) Utilizing immunoassays to determine systemic tomato spotted wilt virus infection for elucidating field resistance in peanut. Crop Protection 25:235-243. DOI: 10.1016/j.cropro.2005.04.015.

Rowland D., Dorner J., Sorensen R., Beasley J. P., Todd J. (2005) Tomato spotted wilt virus in peanut tissue types and physiological effects related to disease incidence and severity. Plant Pathology 54:431-440. DOI: 10.1111/j.1365-3059.2005.01241.x.

DEPOSIT INFORMATION

A deposit of the University of Florida Research Foundation, Inc. proprietary Peanut Cultivar UFT113 disclosed above and recited in the appended claims has been made with the American Type Culture Collection (ATCC), 10801 University Boulevard, Manassas, Va. 20110. The date of deposit was Dec. 21, 2011. The deposit of 2,500 seeds was taken from the same deposit maintained by University of Florida Research Foundation, Inc. since prior to the filing date of this application. All restrictions will be irrevocably removed upon granting of a patent, and the deposit is intended to meet all of the requirements of 37 C.F.R. §§1.801-1.809. The ATCC Accession Number is PTA-12351. The deposit will be maintained in the depository for a period of thirty years, or five years after the last request, or for the enforceable life of the patent, whichever is longer, and will be replaced as necessary during that period.

What is claimed is:

1. A seed of *Arachis Hypogaea* L. peanut cultivar designated UFT113, wherein a representative sample seed of said cultivar was deposited under ATCC accession no. PTA-12351.

2. A peanut plant, or a part thereof, produced by growing the seed of claim 1.

3. A tissue culture produced from protoplasts or cells from the plant of claim 2, wherein said cells or protoplasts are produced from a plant part selected from the group consisting of leaf, pollen, ovule, embryo, cotyledon, hypocotyl, meristematic cell, root, root tip, pistil, anther, flower, seed, pedicel, stem, and petiole.

4. A peanut plant regenerated from the tissue culture of claim 3.

5. A method for producing a peanut seed, said method comprising crossing two peanut plants and harvesting the resultant peanut seed, wherein at least one peanut plant is the peanut plant of claim 2.

6. A peanut seed produced by the method of claim 5.

7. A peanut plant, or a part thereof, produced by growing said seed of claim 6.

8. The method of claim 5, wherein at least one of said peanut plants is transgenic.

9. A method of producing an herbicide resistant peanut plant, wherein said method comprises introducing a gene conferring herbicide resistance into the plant of claim 2.

10. An herbicide resistant peanut plant produced by the method of claim 9.

11. A method of producing a pest or insect resistant peanut plant, wherein said method comprises introducing a gene conferring pest or insect resistance into the peanut plant of claim 2.

12. A pest or insect resistant peanut plant produced by the method of claim 11.

13. A method of producing a disease resistant peanut plant, wherein said method comprises introducing a gene which confers disease resistance into the peanut plant of claim 2.

14. A disease resistant peanut plant produced by the method of claim 13.

15. A method of producing a peanut plant with a desired trait, wherein the method comprises introducing a gene mutation via chemical mutagenesis into the peanut plant of claim 2.

16. A peanut plant produced by the method of claim 15.

17. The peanut plant of claim 2, wherein said plant has increased resistance to tomato spotted wilt virus.

18. A method of introducing the tomato spotted wilt virus resistance trait of peanut cultivar UFT113 into another peanut cultivar, wherein the method comprises:
   a. crossing a UFT113 plant, wherein a representative sample of seed is deposited under ATCC Accession No. PTA-12351, with a plant of another peanut cultivar;
   b. selecting one or more progeny plants that have said trait of tomato spotted wilt virus resistance;
   c. backcrossing the selected progeny plants with either parent peanut cultivar;
   d. selecting for backcross progeny plants that have increased resistance to tomato spotted wilt virus; and
   e. repeating steps (c) and (d) two or more times in succession to produce selected third or higher backcross progeny plants that comprise the trait of tomato spotted wilt virus.

19. A method of introducing a desired trait into peanut cultivar UFT113, wherein the method comprises:
   a. crossing a UFT113 plant, wherein a representative sample of seed is deposited under ATCC Accession No. PTA-12351, with a plant of another peanut cultivar that comprises a desired trait, wherein the desired trait is selected from the group consisting of low pod-splitting, herbicide resistance, insect resistance, modified fatty acid content, modified seed yield, modified oil percent, modified protein percent, modified fancy pod percent, modified pod size, shape, or color, and resistance to bacterial disease, fungal disease or viral disease;
   b. selecting one or more progeny plants that have the desired trait;

c. backcrossing the selected progeny plants with either parent cultivar;

d. selecting for backcross progeny plants that have the desired trait and the tomato spotted wilt virus resistance of peanut cultivar UFT113; and e. repeating steps (c) and (d) two or more times in succession to produce selected third or higher backcross progeny plants that comprise the desired trait and the tomato spotted wilt virus resistance of peanut cultivar UFT113.

20. A peanut plant produced by the method of claim 19.

21. A peanut plant produced by the method of claim 18.

22. The peanut plant of claim 20, wherein the desired trait is disease resistance and the resistance is selected from the group consisting of southern stem rot, late leaf spot, cylindrocladium black rot, *sclerotinia* blight, early leaf spot, tomato spotted wilt virus, and pod rot complex.

23. The peanut plant of claim 20, wherein the desired trait is insect resistance and the insect resistance is selected from the group consisting of thrips, southern corn rootworm, burrowing bug, lesser cornstalk borer, leaf hopper, aphid, and nematode.

24. The peanut plant of claim 20, wherein said plant has commercially acceptable yield.

25. The peanut plant of claim 20, wherein the desired trait is modified fatty acid content and the fatty acids are selected from the group consisting of oleic acid, linoleic acid, and palmitic acid.

26. The peanut plant of claim 20, wherein the desired trait is modified fatty acid content which confers improved oil stability and resistance to oxidative degradation.

27. A method of producing a commodity plant product, comprising obtaining the plant of claim 2, or a part thereof, and producing a commodity plant product from said plant or plant part thereof, wherein the commodity plant product is selected from the group consisting of edible oil, peanut butter, roasted nuts, salted nuts, livestock feed, flour, soaps, and plastics.

* * * * *